(12) United States Patent
Rolke et al.

(10) Patent No.: US 8,491,880 B2
(45) Date of Patent: Jul. 23, 2013

(54) PHARMACEUTICAL FORMULATIONS OF BIODEGRADABLE BIOCOMPATIBLE CAMPTOTHECIN-POLYMER CONJUGATES

(75) Inventors: James Rolke, Beverly, MA (US); Russell C. Petter, Stow, MA (US); Mao Yin, Nedham, MA (US); Aleksandr Yurkovetskiy, Littleton, MA (US); Gui Liu, Lexington, MA (US); Emile Farhan, Dedham, MA (US)

(73) Assignee: Mersana Therapeutics, Inc., Cambridge, MA (US)

( * ) Notice: Subject to any disclaimer, the term of this patent is extended or adjusted under 35 U.S.C. 154(b) by 501 days.

(21) Appl. No.: 12/635,027

(22) Filed: Dec. 10, 2009

(65) Prior Publication Data

US 2010/0179181 A1    Jul. 15, 2010

Related U.S. Application Data

(60) Provisional application No. 61/121,384, filed on Dec. 10, 2008.

(51) Int. Cl.
*A61K 31/4375*    (2006.01)
*A61K 35/00*    (2006.01)
*A61K 39/00*    (2006.01)

(52) U.S. Cl.
USPC ............. 424/78.17; 424/78.32; 514/238

(58) Field of Classification Search
USPC .................. 424/78.17, 78.32; 514/283
See application file for complete search history.

(56) References Cited

U.S. PATENT DOCUMENTS

| | | | |
|---|---|---|---|
| 5,075,222 A | 12/1991 | Hannum et al. | |
| 5,582,172 A | 12/1996 | Papisov et al. | |
| 5,612,037 A | 3/1997 | Huebner et al. | |
| 5,624,803 A | 4/1997 | Noonberg et al. | |
| 5,811,510 A | 9/1998 | Papisov | |
| 5,817,343 A | 10/1998 | Burke | |
| 5,863,990 A | 1/1999 | Papisov | |
| 5,958,398 A | 9/1999 | Papisov | |
| 6,048,837 A | 4/2000 | Friedman et al. | |
| 6,057,431 A | 5/2000 | Ishihara et al. | |
| 6,294,170 B1 | 9/2001 | Boone et al. | |
| 6,822,086 B1 | 11/2004 | Papisov | |
| 7,160,924 B2 | 1/2007 | Kinstler et al. | |
| 7,270,808 B2 | 9/2007 | Cheng et al. | |
| 7,790,150 B2 | 9/2010 | Papisov et al. | |
| 8,101,164 B2 | 1/2012 | Papisov et al. | |
| 8,247,427 B2 | 8/2012 | Papisov et al. | |
| 2002/0082362 A1 | 6/2002 | Brocchini et al. | |
| 2004/0009229 A1* | 1/2004 | Unger et al. | 424/486 |
| 2005/0169968 A1 | 8/2005 | Elmaleh et al. | |
| 2006/0019911 A1 | 1/2006 | Papisov | |
| 2006/0058513 A1 | 3/2006 | Papisov et al. | |
| 2006/0069230 A1 | 3/2006 | Papisov | |
| 2007/0148250 A1 | 6/2007 | Haas et al. | |
| 2007/0190018 A1 | 8/2007 | Papisov | |
| 2008/0019940 A1 | 1/2008 | Papisov | |
| 2009/0148396 A1 | 6/2009 | Akullian et al. | |
| 2010/0035149 A1 | 2/2010 | Fujiwara et al. | |
| 2010/0150832 A1 | 6/2010 | Papisov | |
| 2011/0275700 A1 | 11/2011 | Papisov | |
| 2012/0027680 A1 | 2/2012 | Papisov et al. | |

FOREIGN PATENT DOCUMENTS

| | | |
|---|---|---|
| EP | 0280474 A2 | 8/1988 |
| EP | 0325270 A2 | 7/1989 |
| EP | 0820473 A1 | 1/1998 |
| EP | 1055685 A1 | 11/2000 |
| EP | 1468036 A2 | 10/2004 |
| WO | WO-9605309 A2 | 2/1996 |
| WO | WO-9640912 A1 | 12/1996 |
| WO | WO-9733552 A1 | 9/1997 |
| WO | WO-9930561 A1 | 6/1999 |
| WO | WO-0078355 A2 | 12/2000 |
| WO | WO-0107486 A1 | 2/2001 |
| WO | WO-0110468 A2 | 2/2001 |
| WO | WO-03059988 A2 | 7/2003 |
| WO | WO-2004009082 A1 | 1/2004 |
| WO | WO-2004009774 A2 | 1/2004 |
| WO | WO-2004089311 A2 | 10/2004 |
| wo | WO 2005/023294    * | 3/2005 |
| WO | WO-2005023294 | 3/2005 |
| WO | WO-2010144881 A1 | 12/2010 |

OTHER PUBLICATIONS

Garcia-Carbonero, et al., "Minireview: Current Perspectives on the Clinical Experience, Pharamcology, and Continued Development of the Camptothecins," Clinical Cancer Research, vol. 8, pp. 641-661, Mar. 2002, 21 pages.

International Search Report and Written Opinion of the International Searching Authority for PCT/US09/67505, mailing date Jan. 26, 2010, 11 pages.

Papisov, et al., "Semisynthetic Hydrophilic Polyals," Biomacromolecules, 2006, 6, 2659-2670, 12 pages.

Physical Tests, 788, Particulate Matter in Injections, United States Pharmacopeia, National Formulary USP31-NF25, Voo. 1, p. 311, 2008, 4 pages.

Bruneel et al. "Chemical Modification of Pullulan: 3. Succinoylation." *Polymer*. 35.12(1994):2656-2658.

Endo et al. "Nature of Linkage and Mode of Action of Methotrexate Conjugated With Antitumor Antibodies: Implications for Future Preparation of Conjugates." *Cancer Res.* 48(1988):3330-3335.

Papisov et al. "Novel EPR-Independent Camptothecin Conjugate With Dual-Phase Drug Release: A Blood Pool Effect?" *34th Int. Symp. Controlled Release Bioactive Mat.* (2007).

Papisov et al. "Pharmacokinetics of a Novel Camptothecin Conjugate (PHF-CPT) With Dual-Phase Drug Release." Annual Meeting of SNM. (2007).

(Continued)

*Primary Examiner* — Anoop Singh
*Assistant Examiner* — Anna Falkowitz
(74) *Attorney, Agent, or Firm* — Mintz Levin Cohn Ferris Glovsky and Popeo, P.C.; Ivor R. Elrifi; Heidi A. Erlacher

(57) ABSTRACT

A camptothecin/polymer dual phase drug release system is described that is stable in both liquid and lyophilized states. The polymer contains acetals and/or ketals.

93 Claims, 11 Drawing Sheets

OTHER PUBLICATIONS

Sausville et al. "A Phase 1 Study of the Safety and Tolerability of Intravenous XMT-1001 in Patients With Advanced Dolid Tumors." *Proc. AACR-NCI-EORTC Int. Conf. Mol. Targets Cancer Therapeutics*. (2007). (Abstract146).

Sausville et al. "A Phase 1 study of XMT-1001, A Novel Water Soluble Camptothecin Conjugate, Given as an Intravenous Infusion Once Every Three Weeks to Patients With Advanced Solid Tumors." Proc. AACR-NCI-EORTC Int. I Conf. Mol. Targets Cancer Therapeutics. (Nov. 2009). (Abstract #B52).

Tomlinson et al. "Polyacetal-Doxorubicin Conjugates Designed for pH Dependent Degradation." *Bioconj. Chem.* 14.6(2003):1096-1106.

Yurkovetskiy et al. "Synthesis of a Macromolecular Camptothecin Conjugate With Dual Phase Drug Release." *Mol. Pharmaceutics.* 1(2004):375-382.

Yurkovetskiy et al. "XMT-1001, A Novel Biodegradable Polyacetal Polymer Conjugate of Camptothecin in Clinical Development." *Curr. Bioactive Compounds*. 7(2011):15-20.

Yurkovetskiy et al. "XMT-1001, a Novel Polymeric Camptothecin Pro-Drug in Clinical Development for Patients With Advanced Cancer." *Adv. Drug Deliv. Rev*. 61.13(2009):1193-1202.

* cited by examiner

PHARMACEUTICAL FORMULATIONS OF BIODEGRADABLE BIOCOMPATIBLE CAMPTOTHECIN-POLYMER CONJUGATES

RELATED APPLICATIONS

This application claims priority under 35 U.S.C. §119(e) to U.S. Provisional Application Ser. No. 61/121,384, filed Dec. 10, 2008, which is hereby incorporated in its entirety by reference.

FEDERALLY SPONSORED RESEARCH OR DEVELOPMENT

The U.S. Government may have certain rights in this invention pursuant to Grant Nos. R21-RR14221 and T32 GM07035 awarded by the National Center for Research Resources and the National Institutes of Health.

TECHNICAL FIELD

This application relates to the field of drug delivery systems, and more particularly to formulations for biodegradable biocompatible polymer conjugates.

BACKGROUND

Camptothecin ("CPT") is an alkaloid isolated from the Chinese tree *Camptotheca acuminate*. CPT is a topoisomerase I inhibitor (i.e., deoxyribonucleic acid replication is blocked in cells exposed to CPT) with antineoplastic and antitumor properties. This activity motivated the evaluation of CPT as a chemotherapeutic agent, but development was discontinued when severe and unpredictable dose-limiting toxicities were observed, such as hemorrhagic cystitis in the bladder and diarrhea. Furthermore, direct parenteral administration is limited by CPT's poor solubility.

CPT derivatives and analogs have been similarly disappointing. The carboxylate salt form of CPT is less active and causes severe and unpredictable toxicity. Although two CPT analogs, topotecan (Hycamptin) and irinotecan (CAMPTOSAR®), are approved for clinical use in the United States as anticancer drugs, these analogs are associated with bone marrow suppression and diarrhea. Irinotecan-induced diarrhea can be fatal (Garcia-Carbonero and Supko (2002) *Clin. Cancer Res.* 8:641-661).

In order to mitigate the toxic effects of CPT while maintaining its therapeutic efficacy, formulations and drug release systems have been developed. WO 2005/023294 describes a drug release system that retains the antitumor activity of CPT while limiting toxicity and increasing solubility and plasma half-life by linking CPT to a polymer backbone containing acetals and/or ketals. This polymer backbone is biodegradable and biocompatible. Acetal and ketal polymers are known to degrade in aqueous solution (Papisov et al., *Biomacromolecules* (2005) 6: 2659-70, which is hereby incorporated in its entirety by reference). Furthermore, CPT is attached to the polymer via ester and amide linkages which tend to hydrolyze in solution. These characteristics make storage difficult, particularly storage of aqueous solutions of CPT-polymer conjugate.

Thus, there exists a need in the art for a storage stable formulation of CPT-polymer conjugates that retains the antitumor activity of CPT while limiting toxicity and increasing solubility. Injectable lyophilized solution powder needs to be reconstituted in Sterile Water for Injection USP, or Saline for Injection USP, for infusion. Thus, there is a need for formulations that are rapidly dissolved to minimize preparation time in the hospital or clinic pharmacy.

SUMMARY

A CPT/polymer dual phase drug release system is described that is stable in both liquid and lyophilized states.

Accordingly, the invention provides a pharmaceutical formulation suitable for intravenous administration including a compound of formula I:

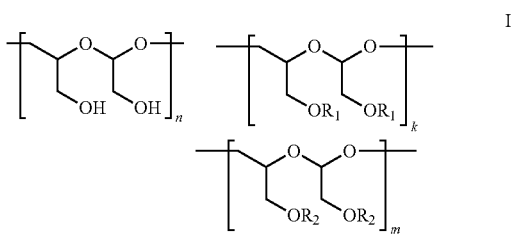

wherein one of $R_1$ is H or

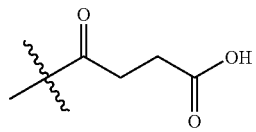 [SMILES: *C(=O)CCC(=O)O]

and the other is

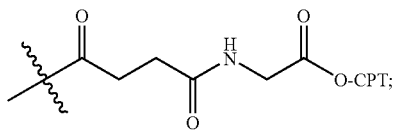

one of $R_2$ is H or

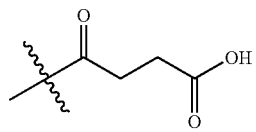 [SMILES: *C(=O)CCC(=O)O]

and the other is

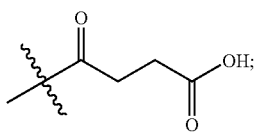 [SMILES: *C(=O)CCC(=O)O]

CPT is camptothecin;
n is 32-3320;
m is 0-833;
k is 1-216; and
wherein k, m, and n are selected so that about 1% to about 15% of the compound by weight is camptothecin;
a stabilizing agent, one or more buffers, and a surfactant;
wherein the molecular weight of the compound is from about 10 kD to about 500 kD.

In addition, the invention provides a storage stable pharmaceutical formulation suitable for intravenous administration including an aqueous solution of a compound of formula I:

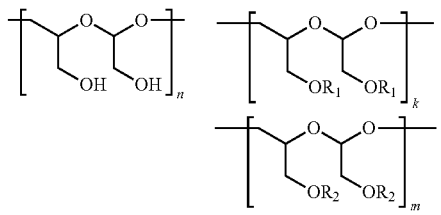
I wherein one of $R_1$ is H or

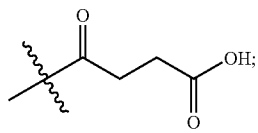 [SMILES: *C(=O)CCC(=O)O]

and the other is

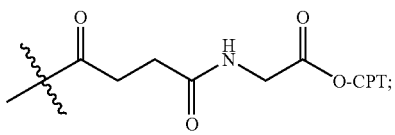

one of $R_2$ is H or

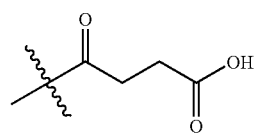 [SMILES: *C(=O)CCC(=O)O]

and the other is

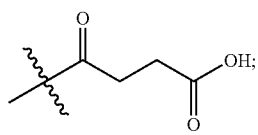 [SMILES: *C(=O)CCC(=O)O]

CPT is camptothecin;
n is 32-3320;
m is 0-833;
k is 1-216; and
    wherein k, m, and n are selected so that about 1% to about 15% of the compound by weight is camptothecin;
a stabilizing agent, one or more buffers, and a surfactant;
wherein the molecular weight of the compound is from about 10 kD to about 500 kD; and
wherein the pH of the pharmaceutical formulation is about 4.2 to about 4.8.

The invention further provides a pharmaceutical formulation suitable for lyophilization and reconstitution including a compound of formula I:

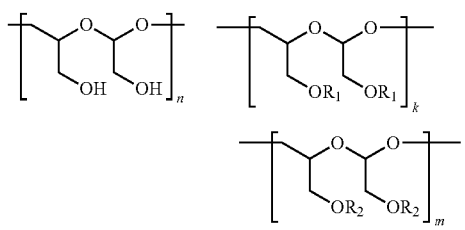
(I)

wherein one of $R_1$ is H or

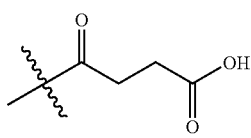 [SMILES: *C(=O)CCC(=O)O]

and the other is

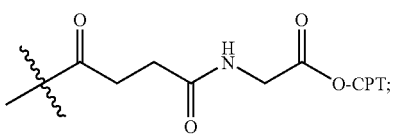

one of $R_2$ is H or

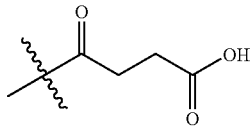 [SMILES: *C(=O)CCC(=O)O]

and the other is

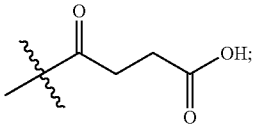 [SMILES: *C(=O)CCC(=O)O]

CPT is camptothecin;
n is 32-3320;
m is 0-833;
k is 1-216; and
    wherein k, m, and n are selected so that about 1% to about 15% of the compound by weight is camptothecin; and
a stabilizing agent, one or more buffers, and a surfactant;
wherein the molecular weight of the compound is from about 10 kD to about 500 kD.

Another aspect of the invention is directed to an injectable solution including a compound of formula I:

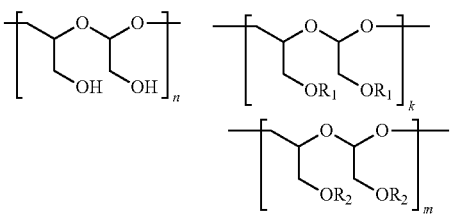

wherein one of $R_1$ is H or

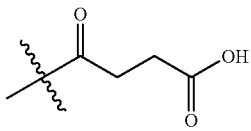 [SMILES: *C(=O)CCC(=O)O]

and the other is

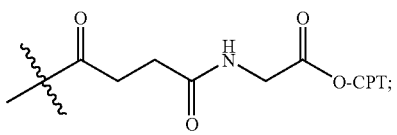

one of $R_2$ is H or

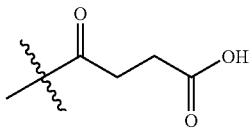 [SMILES: *C(=O)CCC(=O)O]

and the other is

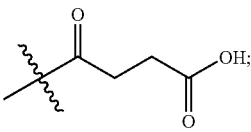 [SMILES: *C(=O)CCC(=O)O]

CPT is camptothecin;
n is 32-3320;
m is 0-833;
k is 1-216; and
    wherein k, m, and n are selected so that about 1% to about 15% of the compound by weight is camptothecin; and
a stabilizing agent, one or more buffers, and a surfactant;
wherein the molecular weight of the compound is from about 10 kD to about 500 kD;
wherein the injectable solution is prepared using a liquid.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In addition, the materials, methods, and examples are illustrative only and not intended to be limiting.

Other features and advantages of the invention will be apparent from the detailed description, drawings, and from the claims.

DETAILED DESCRIPTION

Figure 1:
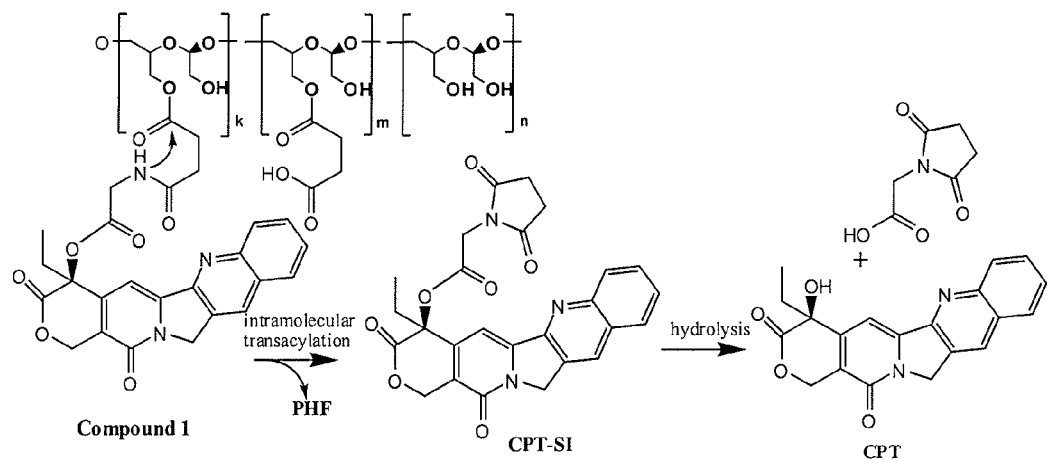
FIG. 1 is a diagram depicting a pathway for release of CPT from the polymer backbone.

Disclosed herein are formulations of camptothecin ("CPT")-polymer conjugates. These formulations provide CPT-polymer conjugates that are stable during extended storage. Further details of suitable CPT-polymer conjugates are provided in Published International Application WO 2005/023294, entitled "Dual Phase Drug Release System," which is hereby incorporated in its entirety by reference.

Definitions

As used herein, a solution is "suitable for intravenous administration" if it is free of particulate matter and is generally clear. Limits for particulate matter occurring in intravenous fluids are defined in the United States Pharmacopeia (National Formulary USP31-NF26, volume 1, page 311, physical tests <788> (2008), which is hereby incorporated in its entirety by reference).

As used herein, a solution is "injectable" if it is suitable for intravenous administration.

As used herein, "stabilizing agents" are excipients added to a solution to optimize lyophilization of the solution and/or to improve stability of the compounds of formula I and formula II in the solution. When lyophilized, a solution containing a suitable stabilizing agent will form a discrete cake that can be easily reconstituted.

As used herein, a solution is "storage stable" if the compounds of formula I and formula II in the solution are stable in the solution for at least 60 days when stored at 2-8° C., i.e., ≧90% of the compounds of formula I and formula II in the solution do not degrade after 60 days when stored at 2-8° C. As used herein, a solution is "highly storage stable" if ≧95% of the compounds of formula I and formula II in the solution do not degrade after 60 days when stored at 2-8° C.

As used herein, a lyophilized cake is "storage stable" if the compounds of formula I and formula II in the lyophilized cake are stable for at least 12 months when stored at 2-8° C., i.e., ≧90% of the compounds of formula I and formula II in the lyophilized cake do not degrade after 13 months when stored at 2-8° C. As used herein, a lyophilized cake is "highly storage stable" if ≧95% of the compounds of formula I and formula II in the lyophilized cake do not degrade after 60 days when stored at 2-8° C.

As used herein in the context of "storage stable," the term "degrade" refers to the amount of the compounds of formula I or formula II at a particular time point compared to time 0, as determined by molecular weight measured by SEC, or as determined by percent total AUC measured by RP-HPLC, using the methods described herein.

As used herein, the phrases "CPT-polymer conjugate," "PHF-CPT conjugate," "conjugate," and "PHF-CPT" refer to compounds of formula I and compounds of formula II.

As used herein, the term "drug loading" refers to the amount of CPT bound to the polymer backbone, and can be indicated by the value of "k" in formula I and formula II; by the ratio of the value of "k" to the values of "m" and "n" in formula I and formula II; or by the ratio of the value of "k" to the values of "k" and "m" and "n" in formula I and formula II. Drug loading may also be expressed in terms of percent CPT by weight of the CPT-polymer conjugate. Drug loading may also be referred to herein as "CPT loading."

1. CPT-Polymer Conjugate

A non-limiting exemplary CPT-polymer conjugate is a compound of formula II, shown below, in which a polymer polyacetal backbone of poly[1-hydroxymethylethylene hydroxymethyl-formal] (PHF) is conjugated to CPT via a succinamidoester linker.

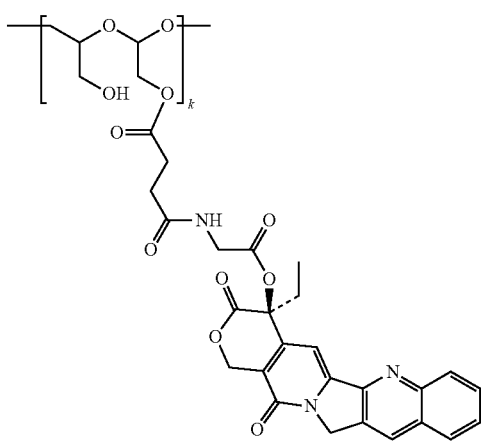

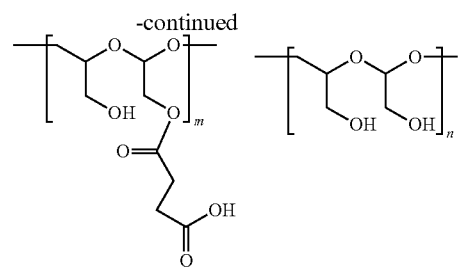

The polymer backbone of the compounds of formula I and formula II consists of three distinct monomer blocks randomly located along the polymer backbone: randomly distributed monomers that include glycerol-glycolaldehyde (monomer block "n"); randomly distributed monomers of glycerol-glycolaldehyde that have been modified by succinylation to form a pendant succinate ester (monomer block "m"); and randomly distributed monomers of glycerol-glycolaldehyde that have been succinylated and then further modified by covalent linkage to CPT-glycinate via an amide bond (monomer block "k"). In one embodiment, the linker between CPT and the polymer backbone monomer block k is succinate-glycinate. The succinate linker is oriented in compounds of formula I and formula II such that an ester linkage is formed at the polymer backbone side, while the opposite carboxyl forms an amide bond with CPT-glycinate.

The CPT-polymer conjugate contains what is referred to as a "dual phase" drug delivery system because it is believed that at least one mode of release of the CPT drug from the polymer backbone occurs in two steps. FIG. 1 illustrates the release of CPT from the polymer backbone in two phases. Without wanting to be limited to any theory, it is believed that first, the nitrogen of the succinamide attacks the nearby ester linking the succinate to the polymer, and that the rate of this reaction increases as temperature and pH increase. The ensuing intramolecular transacylation liberates water insoluble camptothecin-glycinate-succinimide (CPT-SI) from the PHF polyacetal polymer. In the second step, the glycine ester of CPT-SI is hydrolyzed, presumably via an intracellular lipase, to yield CPT and succinimido-glycine as a by-product.

Figure 2:
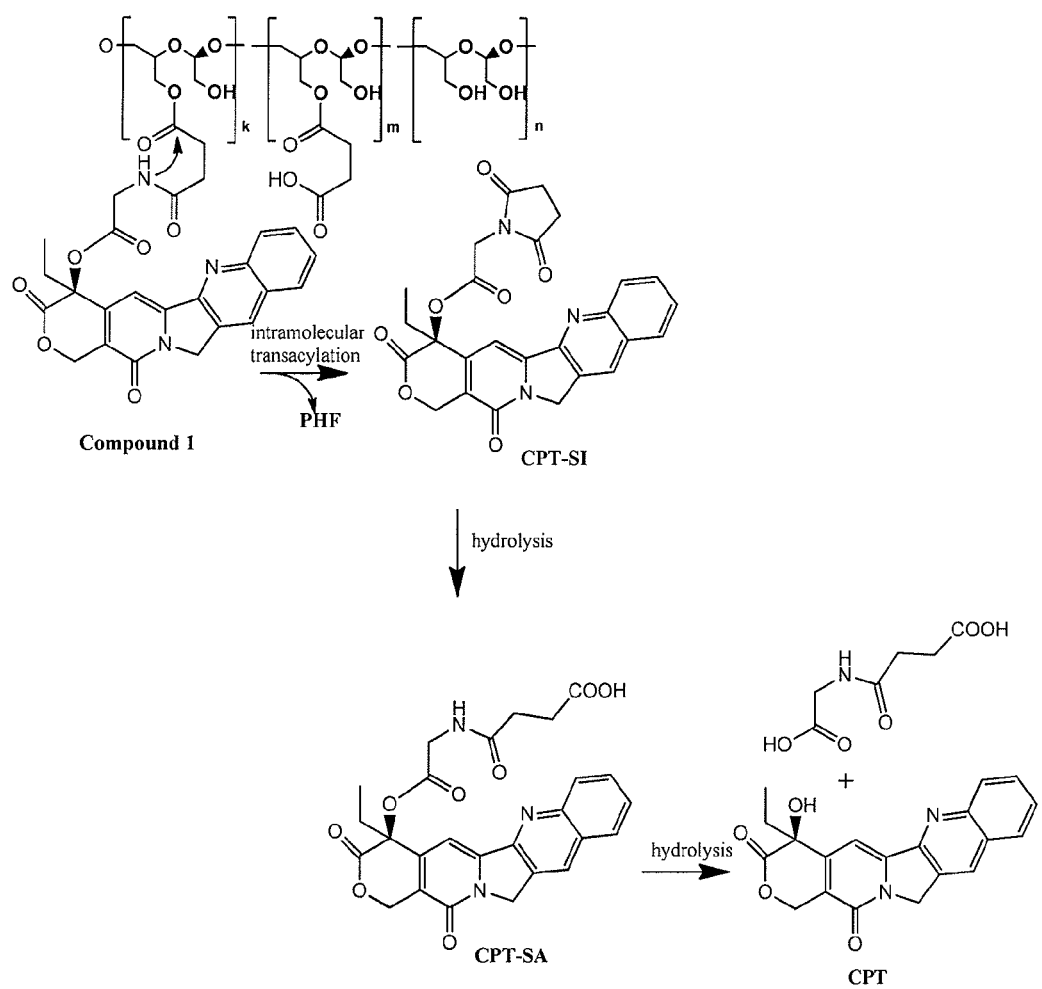
FIG. 2 is a diagram depicting an alternative pathway for release of CPT from the polymer backbone.

CPT may also be released from the polymer conjugate by an alternative three-step pathway shown in FIG. 2. Catalyzed by enzyme or buffer, the succinimide ring of CPT-SI is hydrolyzed to afford camptothecin-succinamide (CPT-SA). Meanwhile, CPT-SA can cyclize to form CPT-SI. Subsequent hydrolysis of the remaining glycine ester liberates CPT.

The polymer backbone contains acetals which tend to hydrolyze at low pH. CPT is attached to the polymer via ester and amide linkages which tend to hydrolyze at high pH. The conjugates therefore have components that are individually destabilized at low pH and high pH.

This possible instability is problematic when storing the CPT-polymer conjugate, particularly as an aqueous solution. At various stages during the manufacturing, storage, and use of a pharmaceutical composition, the CPT-polymer conjugate must be stable in aqueous solution for an extended period of time. For example, it can be necessary to store a formulation containing the CPT-polymer conjugate for up to 60 days in solution before lyophilization. It is desired that the solution demonstrate aqueous stability for a period of time.

2. CPT Loading on PHF Polymer

In one aspect, the drug (CPT) loading of the CPT-polymer conjugate can be adjusted by controlling the level of CPT drug moieties bound to the polymer backbone. While higher levels of drug loading would be expected to deliver a greater amount of drug and therefore to be advantageous in a pharmaceutical formulation, it has been surprisingly discovered that drug formulations having relatively high levels of drug loading (for example, more than about 15% by weight, or in some embodiments more than 7% by weight) do not provide the most advantageous formulation for drug delivery. CPT-polymer conjugates having selected drug loads (for example, in some embodiments about 4% to about 7% by weight), and aqueous solutions thereof, provide several advantages to a pharmaceutical formulation.

In some embodiments, the CPT-polymer conjugates have a weight average molecular weight of between about 10 kD to about 500 kD. In other embodiments, the CPT-polymer conjugates have a weight average molecular weight of between about 45 kD to about 375 kD, between about 55 kD to about 135 kD, or between about 135 kD to about 500 kD. In other embodiments, the CPT-polymer conjugates have a weight average molecular weight of about 10 kD, about 15 kD, about 25 kD, about 35 kD, about 45 kD, about 55 kD, about 75 kD, about 100 kD, about 125 kD, about 135 kD, about 150 kD, about 175 kD, about 200 kD, about 225 kD, about 250 kD, about 275 kD, about 300 kD, about 325 kD, about 350 kD, about 375 kD, about 400 kD, about 425 kD, about 450 kD, about 475 kD, or about 500 kD.

In some embodiments, the CPT-polymer conjugate includes about 32 to about 3320 monomer blocks of n, 0 to about 833 monomer blocks of m, and about 1 to about 216 monomer blocks of k.

The ratio of k to (m+n) is from about 0.0029 to about 0.045. In certain embodiments, the values for 'k', 'm', and 'n' are selected to provide formulations containing a CPT:polymer ratio (i.e., k/(k+m+n)) of between about 0.0029 to about 0.0431. In yet further embodiments, m/(k+m+n) is between about 0 to about 0.167; and n/(k+m+n) is between about 0.787 to about 0.955.

In some embodiments, the CPT-polymer conjugate includes about 200 to about 600 monomer blocks of n, about 300 to about 500 monomer blocks of n, or about 350 to about 450 monomer blocks of n. In other embodiments, the CPT-polymer conjugate includes about 39 to about 3196, about 40 to about 3154, about 500 to about 1000, about 1000 to about 2000, or about 2000 to about 3154 monomer blocks of n. In other embodiments, the CPT-polymer conjugate includes about 300, about 325, about 350, about 375, about 400, about 425, about 450, about 475, or about 500 monomer blocks of n. In other embodiments, the CPT-polymer conjugate includes about 750, about 1000, about 1500, about 2000, about 2500, about 3000, or about 3154 monomer blocks of n.

In some embodiments, the CPT-polymer conjugate includes about 0 to about 60 monomer blocks of m, about 10 to about 50 monomer blocks of m, about 20 to about 40 monomer blocks of m, or about 25 to about 35 monomer blocks of m. In other embodiments, the CPT-polymer conjugate includes about 2 to about 790, about 2 to about 776, about 60 to about 700, about 200 to about 500, or about 300 to about 400 monomer blocks of m. In other the CPT-polymer conjugate includes 0, about 5, about 10, about 20, about 30, about 40, about 50, about 60, about 100, about 200, about 300, about 400, about 500, about 600, or about 700 monomer blocks of m.

In some embodiments, the CPT-polymer conjugate includes about 3 to about 20 monomer blocks of k, about 5 to about 15 monomer blocks of k, or about 7 to about 12 monomer blocks of k. In other embodiments, the CPT-polymer conjugate includes about 1 to about 101, about 1 to about 86, about 20 to about 40, about 40 to about 60, about 60 to about 80, about 80 to about 100, about 100 to about 125, about 125 to about 150, about 150 to about 175, about 175 to about 200, or about 175 to about 216 monomer blocks of k. In some embodiments, the CPT-polymer conjugate includes about 1, about 2, about 3, about 4, about 5, about 6, about 7, about 8, about 9, about 10, about 11, about 12, about 13, about 14, about 15, about 16, about 17, about 18, about 19, or about 20 monomer blocks of k. In some embodiments, the CPT-polymer conjugate includes about 30, about 40, about 50, about 60, about 70, about 80, about 90, about 100, about 110, about 120, about 130, about 140, about 150, about 160, about 170, about 180, about 190, about 200, about 210, or about 216 monomer blocks of k.

In some embodiments, the ratio of $k/(m+n)$ is between about 0.012 and about 0.045, about 0.02 and about 0.035, about 0.015 and about 0.04, or about 0.025 and about 0.03. In some embodiments, the ratio of $k/(m+n)$ is between about 0.0116 and about 0.0205, or about 0.0146 and about 0.0175. In other embodiments, the ratio of $k/(m+n)$ is between about 0.030 and about 0.040, or about 0.035 and about 0.0375. In other embodiments, the of $k/(m+n)$ is about 0.003, about 0.004, about 0.005, about 0.006, about 0.007, about 0.008, about 0.009, about 0.010, about 0.011, about 0.012, about 0.013, about 0.014, about 0.015, about 0.016, about 0.017, about 0.018, about 0.019, about 0.02, about 0.021, about 0.022, about 0.023, about 0.024, about 0.025, about 0.026, about 0.027, about 0.028, about 0.029, about 0.03, about 0.031, about 0.032, about 0.033, about 0.034, about 0.035, about 0.036, about 0.037, about 0.038, about 0.039, about 0.04, about 0.041, about 0.042, about 0.043, about 0.044, or about 0.045.

In some embodiments, the ratio of $k/(k+m+n)$ is between about 0.0115 to about 0.0201, or about 0.0144 to about 0.0172. In some embodiments, the ratio of $k/(k+m+n)$ is about 0.015, about 0.016, about 0.017, about 0.018, about 0.019, about 0.02, about 0.021, about 0.022, about 0.023, about 0.024, about 0.025, about 0.026, about 0.027, about 0.028, about 0.029, about 0.03, about 0.031, about 0.032, about 0.033, about 0.034, about 0.035, about 0.036, about 0.037, about 0.038, about 0.039, about 0.04, about 0.041, about 0.042, about 0.043, about 0.044, or about 0.045.

In some embodiments, the ratio of $m/(k+m+n)$ is about 0.07, about 0.08, about 0.09, about 0.1, about 0.11, about 0.12, about 0.13, about 0.14, about 0.15, about 0.16, or about 0.167. In other embodiments, the ratio of $m/(k+m+n)$ is between about 0.08 and about 0.12, or between about 0.09 and 0.11. In other embodiments, the ratio of $m/(k+m+n)$ is between about 0.07 and about 0.10, about 0.08 and about 0.11, about 0.09 and about 0.012, or about 0.1 and about 0.13. In other embodiments, the ratio of $m/(k+m+n)$ is between about 0.022 to about 0.158, or about 0.025 to about 0.155.

In some embodiments, the ratio of $n/(k+m+n)$ is between about 0.08 and about 0.095, about 0.085 and about 0.090, about 0.86 and about 0.89, about 0.87 and 0.88, about 0.85 and about 0.87, about 0.86 and about 0.88, about 0.87 and about 0.89, or about 0.88 and about 0.9. In other embodiments, the ratio of $n/(k+m+n)$ is about 0.81 to about 0.946, or about 0.813 to about 0.943. In other embodiments, the ratio of $n/(k+m+n)$ is about 0.787, about 0.8, about 0.81, about 0.82, about 0.83, about 0.84, about 0.85, about 0.86, about 0.87, about 0.88, about 0.89, about 0.90, about 0.91, about 0.92, about 0.93, about 0.94, about 0.95, or about 0.955.

In other embodiments, the CPT-polymer conjugate has a distribution of polymer blocks such that about 85% to about 90% by number of the monomer blocks are monomer block n, 7% to about 13% by number of the monomer blocks are monomer block m, and about 2% to about 3% by number of the monomer blocks are monomer block k.

In other embodiments, the CPT-polymer conjugate has a distribution of polymer blocks such that about 85%, about 86%, about 87%, about 88%, about 89%, or about 90% by number of the monomer blocks are monomer block n. In other embodiments, the CPT-polymer conjugate has a distribution of polymer blocks such that about 85% to about 87%, about 86% to about 88%, about 87% to about 89%, or about 88% to about 90% by number of the monomer blocks are monomer block n.

In other embodiments, the CPT-polymer conjugate has a distribution of polymer blocks such that about 7%, about 8%, about 9%, about 10%, about 11%, about 12%, or about 13% by number of the monomer blocks are monomer block m. In other embodiments, the CPT-polymer conjugate has a distribution of polymer blocks such that about 7% to about 9%, about 8% to about 10%, about 9% to about 11%, 10% to about 12%, or about 11% to about 13% by number of the monomer blocks are monomer block m.

In other embodiments, the CPT-polymer conjugate has a distribution of polymer blocks such that about 2%, about 2.1%, about 2.2%, about 2.3%, about 2.4%, about 2.5%, about 2.6%, about 2.7%, about 2.8%, about 2.9%, or about 3% by number of the monomer blocks are monomer block k. In other embodiments, the CPT-polymer conjugate has a distribution of polymer blocks such that about 2% to about 2.2%, about 2.1% to about 2.3%, about 2.2% to about 2.4%, about 2.3% to about 2.5%, about 2.4% to about 2.6%, about 2.5% to about 2.7%, about 2.6% to about 2.8%, about 2.7% to about 2.9%, or about 2.8% to about 3% by number of the monomer blocks are monomer block k.

In other embodiments, k, m, and n are selected so that the CPT-polymer conjugate is about 1% to about 15% CPT by weight. In other embodiments, the CPT-polymer conjugate is about 4% to about 7%, or about 5% to about 6% CPT by weight. In still other embodiments, the CPT-polymer conjugate is about 1% to about 4%, about 7% to about 10%, about 4% to about 12%, or about 10% to about 15% CPT by weight. In still other embodiments, the CPT-polymer conjugate is about 4% to about 5.5%, 4.5% to about 6%, about 5% to about 6.5%, about 5.5% to about 7%, about 6% to about 7.5%, about 6.5% to about 8%, about 7% to about 8.5%, about 7.5% to about 9%, about 8% to about 9.5%, about 8.5% to about 10%, about 9% to about 11%, about 10% to about 12%, about 11% to about 13%, about 12% to about 14%, or about 13% to about 15% CPT by weight. In still other embodiments, the CPT-polymer conjugate is about 1%, about 2%, about 3%, about 4%, about 4.5%, about 5%, about 5.5%, about 6%, about 6.5%, about 7%, about 8%, about 9%, about 10%, about 11%, about 12%, about 13%, about 14%, or about 15% CPT by weight.

In CPT-polymer conjugates of weight average molecular weights of about 10 kD to about 100 kD, PHF-SA has about 30-75 available attachment sites along the polymer backbone. In theory many of these attachment sites can be linked to a CPT drug moiety. It has been discovered that the CPT-polymer conjugate becomes less soluble as the amount of CPT attached to the polymer backbone increases. The selected drug loading of about 4% to about 7% weight/weight CPT/polymer, corresponding to about 10 to about 15 CPT moieties in a polymer having a weight average molecular weight of about 40 kD to about 100 kD, maintains a desirable balance between solubility and activity of the conjugate.

When drug loading is above about 15% by weight, or in some embodiments above about 7% by weight, the hydrophobic CPT molecules may aggregate together forming a micelle-like structure, leaving only the hydrophilic polymer exposed to water. These micelle-like structures may also display reduced efficacy and negatively affect the solution properties of the drug solution. For example, when drug loading is too high, the CPT-polymer conjugate may be difficult to filter through a 0.2 micron filter, requiring the use of tangential flow filtration for sterilization. Overloading may also create non-uniform CPT-polymer conjugate that, even if capable of being filtered, suffers from significant loss of CPT-polymer conjugate that is above the 0.2 micron limit. Furthermore, as drug loading increases, the CPT may form tertiary structures which may cause an immune response in some patients. The particle size of the CPT-polymer conjugate increases as drug loading increases. Large CPT-polymer conjugate particle size may be associated with hypersensitivity reactions.

3. Storage-Stable Aqueous Solution

In one or more aspects, a storage stable aqueous solution suitable for intravenous administration includes a CPT-polymer conjugate at a pH selected to provide storage stability for the CPT-polymer conjugate, and a stabilizing agent. In various embodiments, the storage stable CPT-polymer conjugates include aqueous solutions of CPT-polymer conjugate buffered to a pH of about 4.0 to about 5.0. In other embodiments, the aqueous solutions of CPT-polymer conjugate are buffered to a pH of about 4.2 to about 4.8, or about 4.4 to about 4.6. In other embodiments, the aqueous solutions of CPT-polymer conjugate are buffered to a pH of about 4.0, about 4.1, 4.2, about 4.3, about 4.4, about 4.5, about 4.6, about 4.7, about 4.8, about 4.9, or about 5.0. The aqueous solutions described herein exhibit storage stability. This is surprising, as the polymer of the CPT-polymer conjugates is known to degrade below pH 5.2. The solutions including CPT-polymer conjugates described herein are stable for at least 60 days when stored at 2-8° C.

The aqueous solution including CPT-polymer conjugate may be buffered to the desired pH using conventional buffers. In some embodiments, the buffer is selected from pharmaceutically acceptable buffers. Non-limiting examples of buffers suitable for use with the solutions include one or more of sodium citrate, ascorbate, succinate, lactate, citric acid, boric acid, borax, hydrochloric acid, disodium hydrogen phosphate, acetic acid, formic acid, glycine, bicarbonate, tartaric acid, Tris-glycine, Tris-NaCl, Tris-ethylenediamine tetraacetic acid ("EDTA"), Tris-borate-EDTA, Tris-acteate-EDTA ("TAE") buffer and Tris-buffered saline, 4-(2-hydroxyethyl)-1-piperazineethanesulfonic acid ("HEPES"), 3-(N-morpholino)propanesulfonic acid ("MOPS"), piperazine-1,4-bis (2-ethanesulfonic acid) ("PIPES"), 2-(N-morpholino) ethanesulfonic acid ("MES"), phosphate buffered saline ("PBS"), saline-sodium citrate ("SSC"), saline-tris-EDTA ("STE"), and tris-magnesium. In one embodiment, the storage stable aqueous solution is buffered with a pH 4.0-5.0 buffer solution including sodium citrate dihydrate and about 1 M HCl. In one embodiment, the storage stable aqueous formulation is buffered with a pH 4.5 buffer solution of sodium citrate and citric acid.

In one particular embodiment, or any of the other embodiments described herein, the aqueous solution including CPT-polymer conjugate includes between about 0.1% to about 10%, about 1% to about 9%, or about 2.5% to about 8% sodium citrate by weight. In some embodiments, the aqueous solution including CPT-polymer conjugate includes about 0.1%, about 0.5%, about 0.9%, about 1%, about 1.5%, about 2%, about 2.5%, about 3%, about 3.5%, about 4%, about 4.5%, about 4.8%, about 5%, about 5.5%, about 6%, about 6.5%, about 7%, about 7.5%, about 7.7%, about 7.6%, about 8%, about 8.5%, about 9%, about 9.5%, or about 10% sodium citrate by weight.

In one particular embodiment, or any of the other embodiments described herein, the aqueous solution including CPT-polymer conjugate includes between about 0.1 mg/mL to about 10 mg/mL, about 0.1 mg/mL to about 4.5 mg/mL, or about 0.5 mg/mL to about 5 mg/mL sodium citrate. In some embodiments, the aqueous solution including CPT-polymer conjugate includes about 0.1 mg/mL, about 0.5 mg/mL, about 0.6 mg/mL, about 0.9 mg/mL, about 1 mg/mL, about 1.4 mg/mL, about 1.5 mg/mL, about 2 mg/mL, about 2.5 mg/mL, about 2.8 mg/mL, about 3 mg/mL, about 3.5 mg/mL, about 3.5 mg/mL, about 4 mg/mL, about 4.4 mg/mL, about 4.5 mg/mL, about 5 mg/mL, about 6 mg/mL, about 7 mg/mL, about 8 mg/mL, about 9 mg/mL, or about 10 mg/mL sodium citrate.

In one particular embodiment, or any of the other embodiments described herein, the aqueous solution including CPT-polymer conjugate includes between about 0.1% to about 10%, about 1% to about 9%, or about 2.5% to about 8% citric acid by weight. In some embodiments, the aqueous solution including CPT-polymer conjugate includes about 0.1%, about 0.5%, about 0.9%, about 1%, about 1.5%, about 2%, about 2.5%, about 3%, about 3.5%, about 4%, about 4.2%, about 4.5%, about 4.8%, about 4.9%, about 5%, about 5.5%, about 6%, about 6.5%, about 7%, about 7.5%, about 7.7%, about 7.6%, about 8%, about 8.5%, about 9%, about 9.5%, or about 10% citric acid by weight.

In one particular embodiment, or any of the other embodiments described herein, the aqueous solution including CPT-polymer conjugate includes between about 0.1 mg/mL to about 10 mg/mL, about 0.1 mg/mL to about 4.5 mg/mL, or about 0.5 mg/mL to about 5 mg/mL citric acid. In some embodiments, the aqueous solution including CPT-polymer conjugate includes about 0.1 mg/mL, about 0.5 mg/mL, about 0.6 mg/mL, about 0.9 mg/mL, about 1 mg/mL, about 1.4 mg/mL, about 1.5 mg/mL, about 2 mg/mL, about 2.5 mg/mL, about 2.8 mg/mL, about 3 mg/mL, about 3.5 mg/mL, about 3.5 mg/mL, about 4 mg/mL, about 4.4 mg/mL, about 4.5 mg/mL, about 5 mg/mL, about 6 mg/mL, about 7 mg/mL, about 8 mg/mL, about 9 mg/mL, or about 10 mg/mL citric acid.

This aqueous solution aggregates and sometimes even forms a gel when stored without a stabilizing agent, which renders the CPT-polymer unsuitable for use. While not bound to any particular mode of operation, it is believed that gelling may be due to heavy aggregation. Cross-linking may also occur.

In one particular embodiment, or any of the other embodiments described herein, the aqueous solution including CPT-polymer conjugate further includes a stabilizing agent. The stabilizing agent stabilizes the solution by preventing gelling. Non-limiting examples of stabilizing agents suitable for use with the formulations include sorbitol, mannitol, sucrose, lactose, glucose, xylitol, maltose, hydroxypropyl-β-cyclodextrin, lactitol, dextrose, glycerin, and maltitol. In some embodiments, the stabilizing agent is present in a concentration of about 1 mg/mL to about 500 mg/mL.

In one particular embodiment, or any of the other embodiments described herein, the aqueous solution contains sorbitol at a concentration of about 1 mg/mL to about 500 mg/mL. In other embodiments, the aqueous solution contains sorbitol at a concentration of about 1 mg/mL to about 250 mg/mL, about 50 mg/mL to about 250 mg/mL, or about 250 mg/mL to about 500 mg/mL. In some embodiments, the aqueous solution contains sorbitol at a concentration of about 1 mg/mL, about 25 mg/mL, about 50 mg/mL, about 75 mg/mL, about 95.7 mg/mL, about 100 mg/mL, about 125 mg/mL, about 150 mg/mL, about 175 mg/mL, about 200 mg/mL, about 250 mg/mL, about 300 mg/mL, about 350 mg/mL, about 400 mg/mL, about 450 mg/mL, or about 500 mg/mL.

In one particular embodiment, or any of the other embodiments described herein, the aqueous solution contains sorbitol at a concentration of about 20% to about 90%, about 30% to about 80%, about 40% to about 70%, or about 50% to about 60% by weight. In some embodiments, the aqueous solution contains sorbitol at a concentration of about 20% to about 40%, about 30% to about 50%, about 40% to about 60%, or about 50% to about 70%, about 60% to about 80%, or about 70% to about 90% by weight. In some embodiments, the aqueous solution contains sorbitol at a concentration of about 20%, about 30%, about 40%, about 50%, about 60%, about 70%, about 80%, about 85.8%, or about 90% by weight.

In one particular embodiment, or any of the other embodiments described herein, the aqueous solution contains mannitol at a concentration of about 1 mg/mL to about 500 mg/mL. In other embodiments, the aqueous solution contains mannitol at a concentration of less than 200 mg/mL. In some embodiments, the aqueous solution contains mannitol at a concentration of about 1 mg/mL to about 200 mg/mL, about 1 mg/mL to about 80 mg/mL, about 1 mg/mL to about 25 mg/mL, about 1 mg/mL to about 15 mg/mL, about 4 mg/mL to about 20 mg/mL, about 15 mg/mL to about 50 mg/mL, about 30 mg/mL to about 80 mg/mL, or about 80 mg/mL to about 200 mg/mL. In some embodiments, the aqueous solution contains mannitol at a concentration of about 1 mg/mL, about 2.5 mg/mL, about 4.1 mg/mL, about 4.3 mg/mL, about 5 mg/mL, about 6.3 mg/mL, about 7.5 mg/mL, about 10 mg/mL, about 10.3 mg/mL, about 15 mg/mL, about 20 mg/mL, about 20.3 mg/mL, about 25 mg/mL, about 50 mg/mL, about 75 mg/mL, about 100 mg/mL, about 125 mg/mL, about 150 mg/mL, about 175 mg/mL, about 200 mg/mL, about 250 mg/mL, about 300 mg/mL, about 350 mg/mL, about 400 mg/mL, about 450 mg/mL, or about 500 mg/mL.

In one particular embodiment, or any of the other embodiments described herein, the aqueous solution contains mannitol at a concentration of about 20% to about 90%, about 30% to about 80%, about 40% to about 70%, or about 50% to about 60% by weight. In some embodiments, the aqueous solution contains mannitol at a concentration of about 20% to about 40%, about 30% to about 50%, about 40% to about 60%, or about 50% to about 70%, about 60% to about 80%, or about 70% to about 90% by weight. In some embodiments, the aqueous solution contains mannitol at a concentration of about 20%, about 30%, about 34%, about 34.6%, about 35%, about 40%, about 44.6%, about 50%, about 60%, about 70%, about 80%, about 85.8%, or about 90% by weight.

In one particular embodiment, or any of the other embodiments described herein, the CPT-polymer conjugate is a compound of formula II. In some embodiments, the CPT-polymer conjugate is present in the aqueous solution in an amount up to about 150 mg/mL. In some embodiments, the aqueous solution contains between about 5 mg/mL and about 150 mg/mL, or between about 15 mg/mL and about 50 mg/mL of the CPT-polymer conjugate. In other embodiments, the aqueous solution contains between about 5 mg/mL and about 25 mg/mL, about 20 mg/mL and about 50 mg/mL, about 30 mg/mL and about 60 mg/mL, about 40 mg/mL and about 70 mg/mL, about 50 mg/mL and about 80 mg/mL, about 60 mg/mL and about 90 mg/mL, about 70 mg/mL and about 100 mg/mL, about 80 mg/mL and about 110 mg/mL, about 90 mg/mL and about 120 mg/mL, about 100 mg/mL and about 130 mg/mL, about 110 mg/mL and about 140 mg/mL, and about 120 mg/mL and about 150 mg/mL of the CPT-polymer conjugate. In some embodiments, the aqueous solution contains about 5 mg/mL, about 10 mg/mL, about 15 mg/mL, about 20 mg/mL, about 25 mg/mL, about 30 mg/mL, about 40 mg/mL, about 50 mg/mL, about 60 mg/mL, about 70 mg/mL, about 80 mg/mL, about 90 mg/mL, about 100 mg/mL, about 110 mg/mL, about 120 mg/mL, about 130 mg/mL, about 140 mg/mL, or about 150 mg/mL of the CPT-polymer conjugate.

In one particular embodiment, or any of the other embodiments described herein, the density of the aqueous solution containing a compound of formula II is about 1.0 g/mL to about 1.7 g/mL.

In some embodiments, the aqueous solution may contain additional components. By way of example, the solution may be used in the manufacture of a pharmaceutical formulation and the aqueous solution may contain additives suitable for the manufacturing process. In particular, the solution may include soluble or insoluble additives used in lyophilization of a CPT-polymer conjugate. In one or more embodiments, the aqueous solution may contain soluble or insoluble additives typically found in pharmaceutical formulations. Non-limiting examples of additives useful with the aqueous solutions of the present disclosure include pharmaceutically acceptable excipients such as surfactants, anti-humiditants, anti-oxidants, viscosifiers, salts, and preservatives. In one or more embodiments, the aqueous solution may contain a surfactant or a mixture of surfactants including but not limited to Polysorbate 80, Polysorbate 20, Poloxamer 407, Solutol HS 15, Poloxamer 188, sodium lauryl sulphate, ether sulphates, sulphated oils, cetrimide BP, benzalkonium chloride, lecithin, cetromacrogel 1000 BPC, and alkali metal soaps of the formula RCOOX where R=C10-C20 alkyl group, and X=sodium, potassium, or ammonium.

In one particular embodiment, or any of the other embodiments described herein, the aqueous solution contains Polysorbate 80 at a concentration of between about 0.05% to about 20% by weight. In some embodiments, the aqueous solution contains Polysorbate 80 at a concentration of about 0.05%, about 0.5%, about 1%, about 2%, about 2.5%, about 2.7%, about 3%, about 3.5%, about 4%, about 4.5%, about 5%, about 6%, about 7%, about 8%, about 9%, about 10%, about 15%, or about 20% by weight. In other embodiments, the aqueous solution contains Polysorbate 80 at a concentration of between about 0.05% to about 10%, about 0.75% to about 5%, about 0.5% to about 3%, about 1% to about 2.7%, about 5% to about 15%, or about 10% to about 20% by weight.

In one particular embodiment, or any of the other embodiments described herein, the aqueous solution contains Polysorbate 80 at a concentration of between about 0.1 mg/mL to about 10 mg/mL, about 0.1 mg/mL to about 4.5 mg/mL, about 0.5 mg/mL to about 5 mg/mL, or about 0.1 mg/mL to about 1 mg/mL Polysorbate 80. In some embodiments, the aqueous solution contains Polysorbate 80 at a concentration of about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1 mg/mL, about 1.5 mg/mL, about 2 mg/mL, about 2.5 mg/mL about 3 mg/mL, about 3.5 mg/mL, about 3.5 mg/mL, about 4 mg/mL, about 4.5 mg/mL, about 5 mg/mL, about 6 mg/mL, about 7 mg/mL, about 8 mg/mL, about 9 mg/mL, or about 10 mg/mL Polysorbate 80.

In one particular embodiment, or any of the other embodiments described herein, the aqueous solution may contain up to 1% of a preservative or a mixture of preservatives including but not limited to benzyl alcohol, sodium benzoate acid, sodium nitrate, sulphur dioxide, sodium sorbate and potassium sorbate.

In one particular embodiment, or any of the other embodiments described herein, the aqueous solution is sterile. Filtration is a non-limiting example of sterilization methods useful with the aqueous solution. In some embodiments, the aqueous solution is sterilized by filtration through a 0.1 micron filter and/or a 0.2 micron filter.

4. Lyophilized Formulations

In one aspect, a lyophilized pharmaceutical formulation of the CPT-polymer conjugate in dry powdered or dry cake form is provided. In some embodiments, the lyophilized formulation includes a CPT-polymer conjugate with a CPT:polymer ratio (i.e., k/(k+m+n)) of about 0.0125 to about 0.05. In other embodiments, the lyophilized formulation includes a CPT-polymer conjugate with a CPT:polymer ratio of about 0.015 to about 0.045, about 0.02 to about 0.04, about 0.025 to about 0.035, or about 0.0275 to about 0.03. In other embodiments, the lyophilized formulation includes a CPT-polymer conjugate with a CPT:polymer ratio of about 0.0125 to about 0.03, about 0.02 to about 0.0375, about 0.03 to about 0.0475, or about 0.0325 to about 0.05.

In one particular embodiment, or any of the other embodiments described herein, the lyophilized formulation contains about 50% to about 55% CPT-polymer conjugate by weight. In some embodiments, the lyophilized formulation contains about 50%, about 50.5%, about 51%, about 51.5%, about 52%, about 52.5%, about 53%, about 53.5%, about 54%, about 54.5%, or about 55% CPT-polymer conjugate by weight. In other embodiments, the lyophilized formulation contains about 2% to about 4% CPT by weight. In some embodiments, the lyophilized formulation contains about 2%, about 2.1%, about 2.2%, about 2.3%, about 2.4%, about 2.5%, about 2.6%, about 2.7%, about 2.8%, about 2.9%, about 3%, about 3.1%, about 3.2%, about 3.3%, about 3.4%, about 3.5%, about 3.6%, about 3.7%, about 3.8%, about 3.9% or about 4% CPT by weight.

Pharmaceutical compositions are often lyophilized for transport and are reconstituted immediately before use. However, the CPT-polymer conjugate described herein tends to irreversibly agglomerate during lyophilization and is difficult to reconstitute. For example, lyophilized CPT-polymer without a stabilizing agent is very difficult to reconstitute in water. In some embodiments, the lyophilized formulation contains a stabilizing agent that allows the lyophilized formulation to be reconstituted. Non-limiting examples of stabilizing agents suitable for use with the lyophilized formulations include sorbitol, mannitol, sucrose, lactose, glucose, xylitol, maltose, hydroxypropyl-β-cyclodextrin, and lactitol.

In one particular embodiment, or any of the other embodiments described herein, the lyophilized formulation contains about 80% to about 90% sorbitol by weight. In some embodiments, the lyophilized formulation contains sorbitol in ranges of about 80% to about 82%, about 82% to about 84%, about 84% to about 86%, about 86% to about 88%, or about 88% to about 90% by weight. In some embodiments, the lyophilized formulation contains sorbitol in ranges of about 80% to about 83%, about 82% to about 85%, about 84% to about 87%, or about 86% to about 90% by weight. In some embodiments, the weight percentage of sorbitol in the lyophilized formulation is about 80%, about 81%, about 82%, about 83%, about 84%, about 85%, about 85.8%, about 86%, about 87%, about 88%, about 89%, or about 90% by weight.

In one particular embodiment, or any of the other embodiments described herein, the lyophilized formulation contains about 30% to about 50% mannitol by weight. In some embodiments, the weight percentage of mannitol in the lyophilized formulation is about 30% to about 40%, about 35% to about 45%, or about 40% to about 50% by weight. In some embodiments, the weight percentage of mannitol in the lyophilized formulation is about 30%, about 31%, about 32%, about 33%, about 34%, about 35%, about 36%, about 37%, about 38%, about 39%, about 40%, about 41%, about 42%, about 43%, about 43%, about 44%, about 45%, about 46%, about 47%, about 48%, about 49%, or about 50%. In other embodiments, the weight percentage of mannitol in the lyophilized formulation is about 34.5% by weight or about 44.6% by weight.

In one particular embodiment, or any of the other embodiments described herein, the lyophilized formulations are dissolved immediately when the formulations contain a stabilizing agent and about 0.5% to about 10% of one or more surfactants by weight. Non-limiting examples of surfactants suitable for use with the lyophilized formulations include Polysorbate 80, Polysorbate 20, Poloxamer 407, Solutol HS 15, and Poloxamer 188. In one or more embodiments, the aqueous solution may contain a preservative or a mixture of preservatives including but not limited to benzyl alcohol, sodium benzoate acid, sodium nitrate, sulphur dioxide, sodium sorbate and potassium sorbate.

In one particular embodiment, or any of the other embodiments described herein, the lyophilized formulation contains less than about 4% water by weight. Therefore, in some embodiments the lyophilized formulation is buffered to a pH of about 4.0 to about 5.0 In other embodiments the lyophilized formulation is buffered to a pH of about 4.2 to about 4.8, or a pH of about 4.4 to about 4.6. In some embodiments, the lyophilized formulation is buffered to a pH of about 4.2, about 4.3, about 4.4, about 4.5, about 4.6, about 4.7, or about 4.8.

Non-limiting examples of buffers suitable for use with the formulations include one or more of sodium citrate, ascorbate, succinate, lactate, citric acid, boric acid, borax, hydrochloric acid, disodium hydrogen phosphate, acetic acid, formic acid, glycine, bicarbonate, tartaric acid, Tris-glycine, Tris-NaCl, EDTA, TAE buffer and Tris-buffered saline, HEPES, MOPS, PIPES, MES, and PBS. The buffer may be selected to provide pH stability in both the storage stable aqueous solution prior to lyophilization and the lyophilized dry formulation.

In one particular embodiment, or any of the other embodiments described herein, the lyophilized formulation contains between about 1% to about 10%, about 2% to about 9%, and about 4% to about 7% sodium citrate by weight. In some embodiments, the lyophilized formulation contains about 1%, about 1.5%, about 2%, about 2.5%, about 3%, about 3.5%, about 4%, about 4.5%, about 5%, about 5.5%, about 6%, about 6.5%, about 7%, about 8%, about 9%, or about 10% sodium citrate by weight.

In one particular embodiment, or any of the other embodiments described herein, the lyophilized formulation contains between about 1% and about 10%, about 2% and about 9%, and about 3% and about 5% citric acid by weight. In other embodiments, the lyophilized formulation contains about 1%, about 2%, 3%, 4%, 4.2%, 5%, 6%, 7%, 8%, 9%, or 10% citric acid by weight.

In other embodiments, the lyophilized formulation contains about 6.5% sodium citrate and 4.2% citric acid by weight.

5. Solution for Intravenous Administration

In another aspect, the lyophilized formulation is suitable for intravenous administration after reconstitution with sterile water for injection or 0.9% Normal sodium chloride (saline) for injection USP. In one embodiment, about 695 mg of the lyophilized formulation is reconstituted with about 15 mL sterile water for injection, resulting in an isotonic solution with an osmolality of about 219 mOsmol/kg. In one embodiment, about 695 mg of the lyophilized formulation is reconstituted with about 10 mL sterile water for injection, resulting in an isotonic solution with an osmolality of about 333 mOsmol/kg. In another embodiment, about 168 mg of the lyophilized formulation is reconstituted with about 10 mL of 0.9% sodium chloride for injection USP, resulting in an isotonic solution with an osmolality of about 331 mOsmol/kg. In other embodiment, about 260 mg of the lyophilized formulation is reconstituted with 10 mL of 0.45% sodium chloride for injection USP, resulting in an isotonic solution with an osmolality of about 302 mOsmol/kg.

In some embodiments, after reconstitution, the reconstituted material contains sodium citrate at a concentration of about 0.5 mg/mL to about 3.0 mg/mL and citric acid at a concentration of about 0.3 mg/mL to about 2.0 mg/mL.

EXAMPLES

The invention is further illustrated by the following examples. The examples are provided for illustrative purposes only. They are not to be construed as limiting the scope or content of the invention in any way.

Methods

The following methods were used in the Examples:

Reverse Phase HPLC(RP-HPLC)

The total concentration of free CPT (and impurities) was measured by injecting samples and a set of CPT standards. Analytes were separated by their retention within the column and measured for total area under the curve by UV absorption at 360 nm. A calibration curve was generated using standards of CPT, CPT-SA, and CPT-SI, and this was used to quantify the level of free CPT and associated intermediates in the sample. Results are presented as % AUC, where the AUC of free CPT (or a particular impurity such as CPT-SA or CPT-SI) is divided by the AUC of PHF-CPT. Alternatively, results are presented as % mass, where the mass of free CPT (or a particular impurity) is divided by the mass of PHF-CPT.

Preparation of CPT-SA Standard

CPT-Gly-TFA (50 mg, 0.096 mmol) and succinic anhydride (18 mg, 0.190 mmol) were dissolved in 2 mL of anhydrous pyridine. After an 18 hour agitation at ambient temperature, pyridine was removed in vacuum. The solid residue was suspended in deionized water and extracted with methylene chloride, washed with 0.01 N HCl and dried over magnesium sulfate. Solvent removal in vacuum resulted in a light-yellow solid (41.4 mg, 85% yield) containing >90% CPT-SA (HPLC with 360 nm detection). LC-MS: m/z 506.2 (M+H).

Preparation of CPT-SI Standard

PHF-CPT (500 mg) was dissolved in 10 mL of 0.1 M phosphate pH 7.6 and incubated for 24 hours at 37° C. The resultant suspension was diluted to 150 mL and extracted with methylene chloride (3×150 mL). Methylene chloride layers were combined, washed with 0.01 N HCl, and dried over magnesium sulfate. Solvent was removed in vacuum. The light yellow residue was re-dissolved in methylene chloride, filtered and dried in vacuum to yield 38 mg of a product containing, according to RP-HPLC, 93% CPT-SI.

$^1$H NMR (300 MHz, CDCl$_3$): δ 1.01 (τ, 3H, J=7.4 Hz, C19), δ 2.05-2.32 (m, 2H, C18), δ 2.66 (s, 4H, succinimide), δ 4.32-4.51 (AB, 2H, 17.2 Hz, C-α Gly), δ 5.32 (s, 2H, C-5), δ 5.29-5.65 (AB, 2H, 17.3 Hz, C-17), δ 7.20 (s, 1H, C-14), δ 7.60 (t, 1H, J=7.5 Hz, C-11), δ 7.76 (t, 1H, J=7.7 Hz), δ 7.86 (d, 1H, J=8.3, C-12), δ 8.20 (d, 1H, J=8.3, C-9), δ 8.32 (s, 1H, C-7).

¹³C NMR: 7.23, 28.36, 29.89, 32.04, 39.53, 50.17, 67.31, 77.45, 96.29, 120.54, 128.23, 128.33, 128.64, 130.00, 130.80, 131.35, 145.14, 146.70, 149.08, 152.46, 157.48, 166.27, 166.78, 175.95.

Nuclear Magnetic Resonance (NMR)

NMR was used to verify the amide linkage between succinate and glycine-CPT and to determine the amount of CPT loaded onto the polymer backbone.

UV Assay for Measurement of CPT Loading Rate

CPT loading rate was determined by measuring the optical density at 289 nm and the background correction was set at 500 nm. The UV absorbance maximum of 289 nm is used because the extinction coefficients for all free and polymer bound O(20)-CPT derivatives are essentially the same. From these data, the amount of bound CPT equivalents/mL was determined by calculation using the extinction coefficient. The CPT equivalents/mg were then calculated by dividing by the total concentration of CPT-polymer conjugate in solution as measured by dry weight analysis using lyophilization.

Concentration of Sorbitol (mg/mL)

The concentration of sorbitol in aqueous solutions of CPT-polymer conjugate was determined by comparison to a USP sorbitol external reference standard using cation-exchange HPLC with refractive index ("RI") detection.

Concentration of Mannitol (mg/mL)

The concentration of mannitol in aqueous solutions of CPT-polymer conjugate was determined by comparison to a USP mannitol external reference standard using cation-exchange HPLC with RI detection.

Concentration of Sodium Citrate (mg/mL)

The concentration of sodium citrate dihydrate in aqueous solutions of CPT-polymer conjugate was determined by comparison to a USP citric acid reference standard external standard using reverse phase ion pairing HPLC with UV detection.

Concentration of Unbound Succinic Acid (mg/mL)

The concentration of unbound succinic acid in aqueous solutions of CPT-polymer conjugate was determined using reverse phase anion-exchange HPLC with UV detection. The UV detector was set at 200 nm. The level of unbound succinic acid in the sample was quantified by comparison to a succinic acid calibration curve (Sigma-Aldrich, St. Louis, Mo.).

Molecular Weight Distributions (Mw, D90, D50, D10)

The molecular weight distributions of the CPT-polymer conjugate as well as PHF and PHF-SA were measured by high pressure size exclusion chromatography (HPSEC) with RI detection. Pullulan polysaccharide polymers (Polymer Laboratories, Amherst, Mass.) were used to generate a standard curve. Molecular weight distributions (weight average molecular weight ("Mw"), D90, D50, D10) were calculated based on the polysaccharide standard curve.

Osmolality

The osmolality of aqueous solutions of CPT-polymer conjugate was measured by a vapor pressure osmometer (Vapor).

Method for Measuring Reconstitution Time

A needle was inserted in the center of the rubber stopper until the tip of the needle was just below the stopper to avoid pressure build-up in the vial. Then the sample was reconstituted by removing the flip-top from the vial and adding diluent using a syringe. The pressure release needle and the syringe were removed, and the vial was gently inverted until the contents dissolved. The time required for dissolution was recorded to the whole second using a stopwatch.

Production of Aqueous PHF-CPT Conjugate

Figure 5:
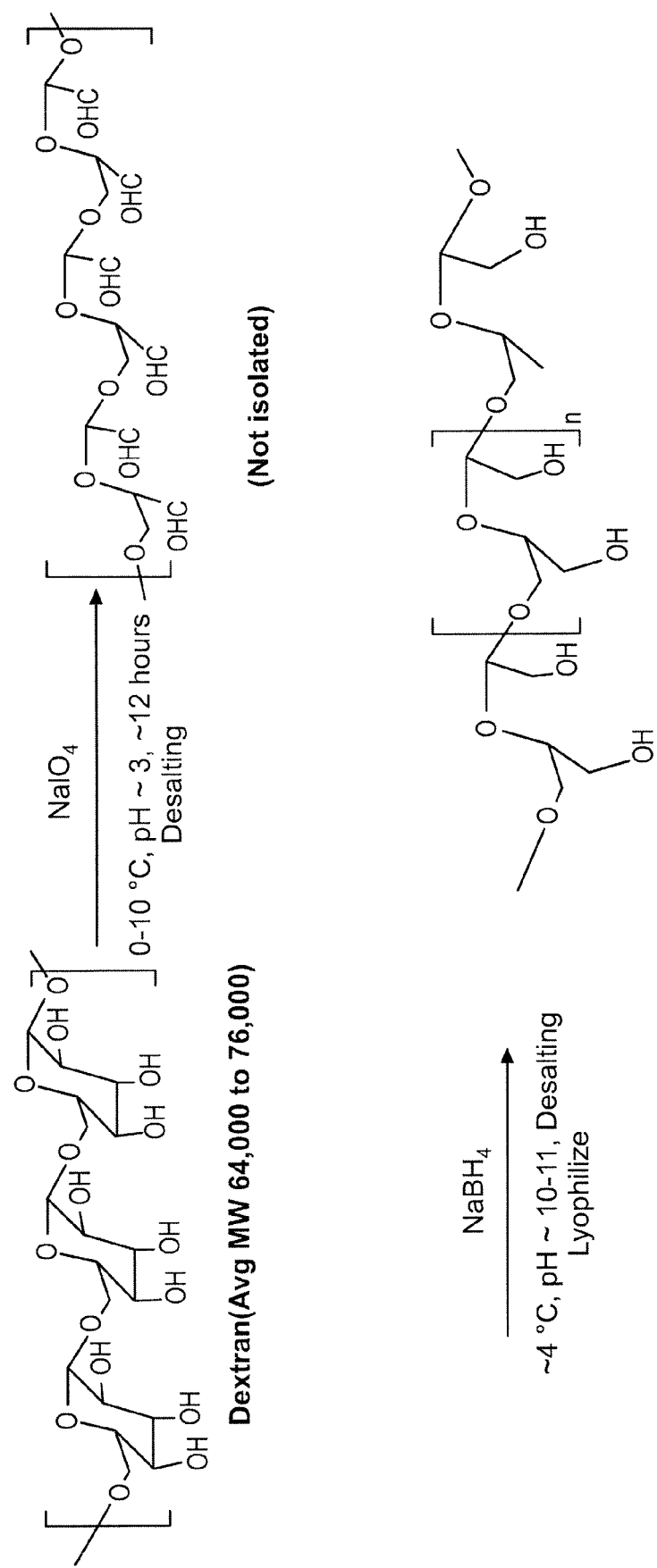
FIG. 5 is a diagram illustrating the synthesis of poly[1-hydroxymethylethylene hydroxymethyl-formal] ("PHF").

Phase 1—Synthesis of Poly [Hydroxymethylethylene Hydroxymenthlformal] "PHF" (FIG. 5)

Dextran was subjected to exhaustive oxidation in aqueous $NaIO_4$ as described in Papisov et al., *Biomacromolecules* (2005) 6: 2659-70, to yield a polymeric poly-aldehyde in which the carbon at position 3 of each glucose residue has been extruded as formate. The oxidized dextran was desalted first by vacuum filtration to remove precipitated inorganic salts and then by tangential flow filtration ("TFF") or membrane diafiltration using a filter having a nominal molecular weight cut off (MWCO) of 10 kD. The poly-aldehyde was then reduced exhaustively using aqueous $NaBH_4$ to yield PHF, which was then desalted by TFF or membrane diafiltration using a filter having a nominal MWCO of 10,000 Daltons. The purified PHF was 0.2 micron filtered and lyophilized in bulk and stored at 2° C. to 8° C. until needed in Phase 4.

Figure 6:
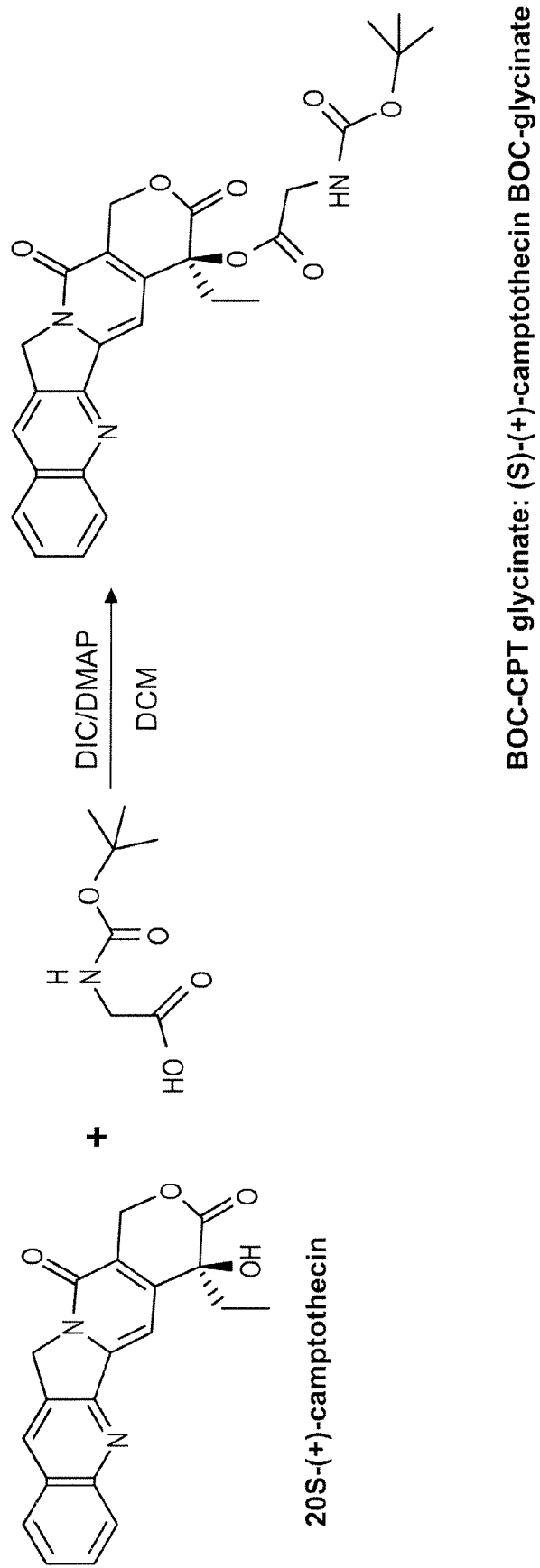
FIG. 6 is a diagram illustrating the synthesis of CPT-glycine-tert-butyloxycarbonyl ("CPT-Gly-BOC").

Phase 2—Synthesis of Camptothecin-Glycine-Tert-Butyloxycarbonyl ("CPT-Gly-BOC") (FIG. 6)

The tertiary alcohol of CPT formed an ester in the presence of BOC-glycine and diisopropyl carbodiimide (DIC), which was subsequently purified by a series of extractions in concentrated sodium bicarbonate solution, distillations, recrystallizations in methanol, and drying under vacuum as per the method described in WO 2005/023294. The purified CPT-Gly-BOC was stored in bulk at 2° C. to 8° C. until needed in Phase 3.

Figure 7:
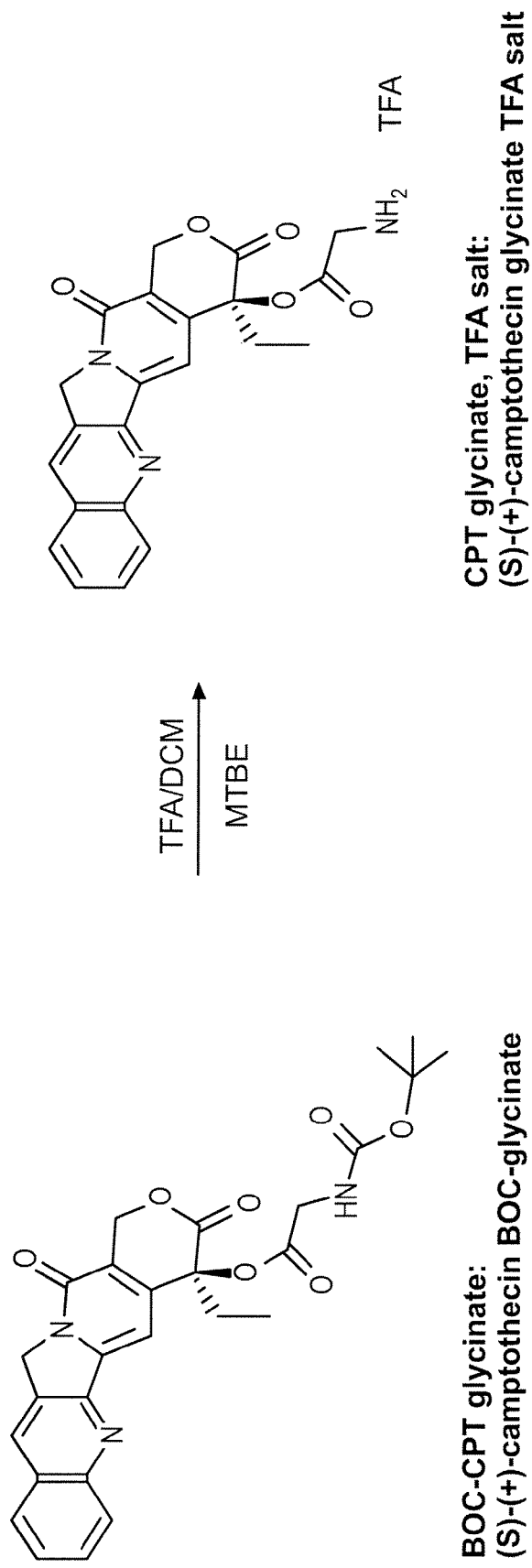
FIG. 7 is a diagram illustrating the synthesis of CPT-glycine-trifluoroacetic acid ("CPT-Gly-TFA").

Phase 3 Synthesis of Camptothecin-Glycine-Trifluoroacetic Acid ("CPT-Gly-TFA") (FIG. 7)

The BOC protecting group was removed using trifluoroacetic acid ("TFA") in methylene chloride at room temperature and CPT-glycinate was isolated as a TFA salt, which was purified by precipitation from diethyl ether, filtration through filter paper, washing with ether, and drying under vacuum as per the method described in WO 2005/023294. The purified CPT-glycine-TFA was stored in bulk at −18° C. to −25° C. until needed in Phase 5.

Figure 8:
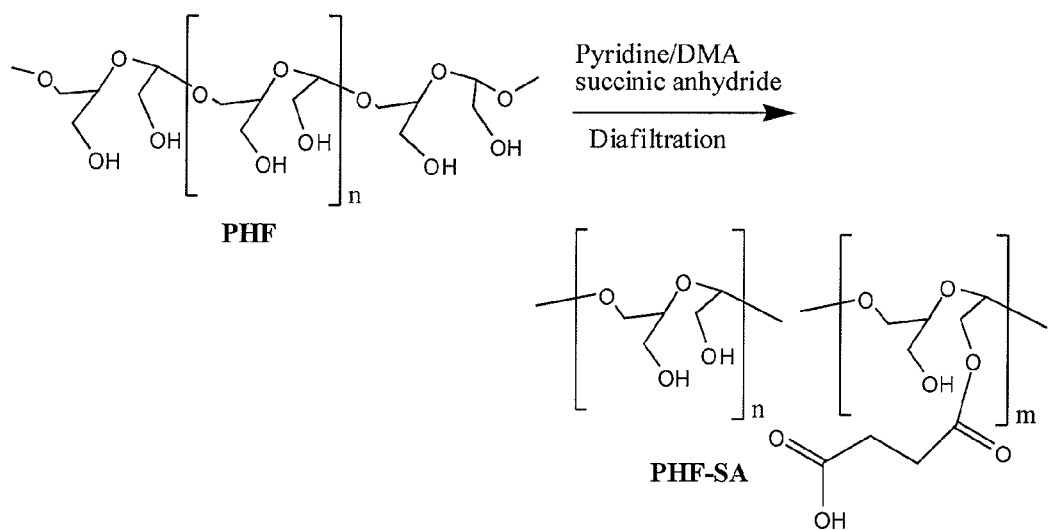
FIG. 8 is a diagram illustrating the synthesis of poly [hydroxymethylethylene hydroxymethylformal]-succinic acid ("PHF-SA").

Phase 4—Synthesis of Poly [Hydroxymethylethylene Hydroxymethylformal]-Succinic Acid ("PHF-SA") (FIG. 8)

PHF (10.00 g, 75.6 mmol), succinic anhydride (0.76 g, 7.6 mmol) and DMAP (1.2 mg, 0.01 mmol) were dissolved in 5 mL of anhydrous pyridine. After 18 hours of agitation at 40° C., the pyridine was removed in vacuum, and the residue was suspended in deionized water. The extent of succinylation was approximately 10 mole percent of the available alcohol groups. The PHF-SA was then desalted by TFF or membrane diafiltration using a filter having a nominal MWCO of 10,000 Daltons. The purified PHF-SA was 0.1 micron filtered and stored in bulk at 2° C. to 8° C. until needed in Phase 5.

Figure 9:
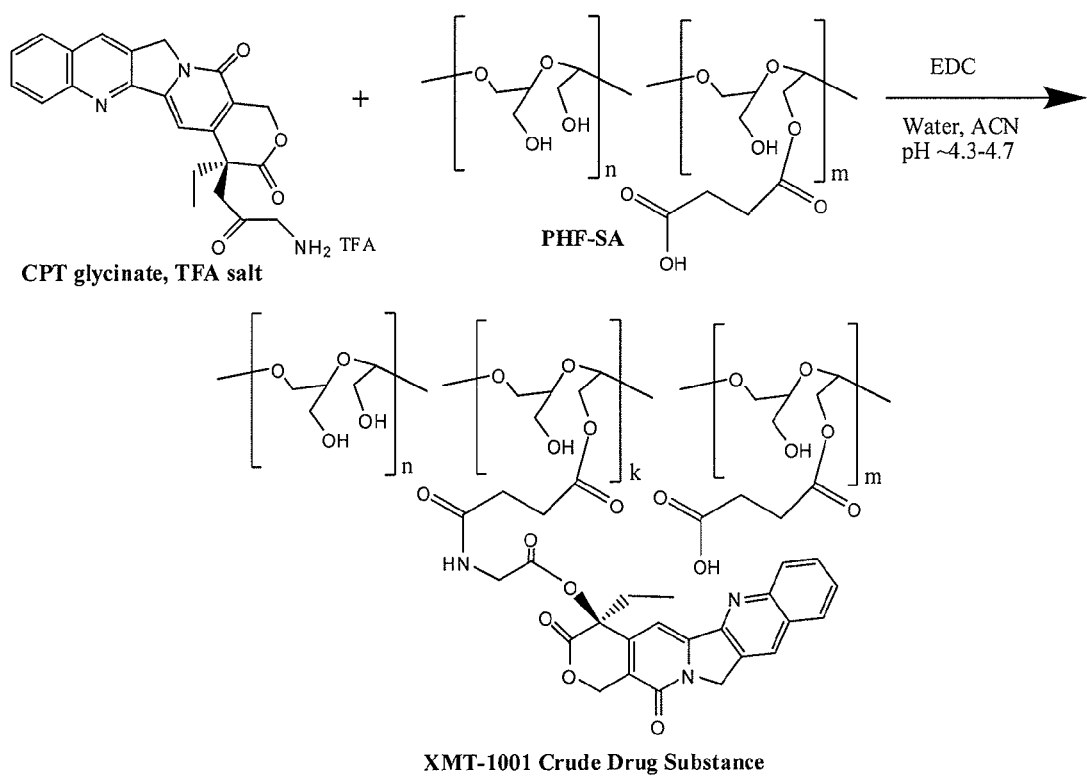
FIG. 9 is a diagram illustrating the coupling of PHF-SA and CPT-Gly-TFA.

Phase 5—Coupling of PHF-SA and CPT-Glycine-TFA (FIG. 9)

The succinates of PHF-SA were activated using ethyl dimethylaminopropyl carbodiimide (EDC) and coupled with CPT-glycine to yield crude aqueous conjugate. PHF-SA (15.0 g, 10.7 mmol SA) was dissolved in 150 mL of deionized water and mixed with 30 mL of dimethylformamide ("DMF"), cooled to −2° C., and combined with CPT-Gly.TFA solution (2.0 g/13.85 mmol in 20 mL of 3:1 acetonitrile/water mixture). Under intense agitation, EDC (2.0 g) was added to the reaction mixture portionally. The pH was adjusted to 5.9-6.0. After 30 minutes of agitation, the temperature of the reaction mixture was brought to ambient, and agitation was continued for another 3 hours. The CPT was monitored by RP-HPLC (UV at 360 nm). The pH was adjusted to 5.5 to prevent CPT release from the conjugate, and the reaction mixture was stored overnight at 8° C. The mixture was then diluted with DMF and water to 600 mL (DMF content 10% v/v), and the conjugate was desalted on Sephadex G-25, lyophilized, and stored at −20° C. The product was an off-white to pale-yellow solid with CPT content of 7.48% w/w (as determined spectrophotometrically at 360 nm). Yield based on CPT content was 80%.

Alternate Phase 5—Coupling of PHF-SA and CPT-Glycine-TFA by a Modified Method

PHF-SA (7.0 g) was dissolved in 150 mL of deionized water and mixed with 30 mL of actonitrile, cooled to 0-5° C., and combined with CPT-Gly.TFA solution (0.9 g/1.73 mmol in 7 ml of acetonitrile). After the pH was adjusted to 5.9-6.0, a solution of EDC (1.0 g) in 5 mL acetonitrile and several drops of deionized water was dropped into the reaction mixture under intense agitation. After 30 minutes of agitation, the temperature of the reaction mixture was brought to ambient temperature, and agitation was continued for another 3 hours. During the reaction, the pH was monitored and adjusted consistently to 5.9-6.0. The CPT conversion was monitored by RP-HPLC (UV at 360 nm). The pH was adjusted to 4.5, filtered through a 0.2 μm filter, and then purified on Sephadex G-25 or by diafiltration (10 kD MWCO). CPT loading was 6.19% by weight. PHF-CPT synthesized by this method was more uniform that synthesized by above method (FIG. 12).

Figure 10:
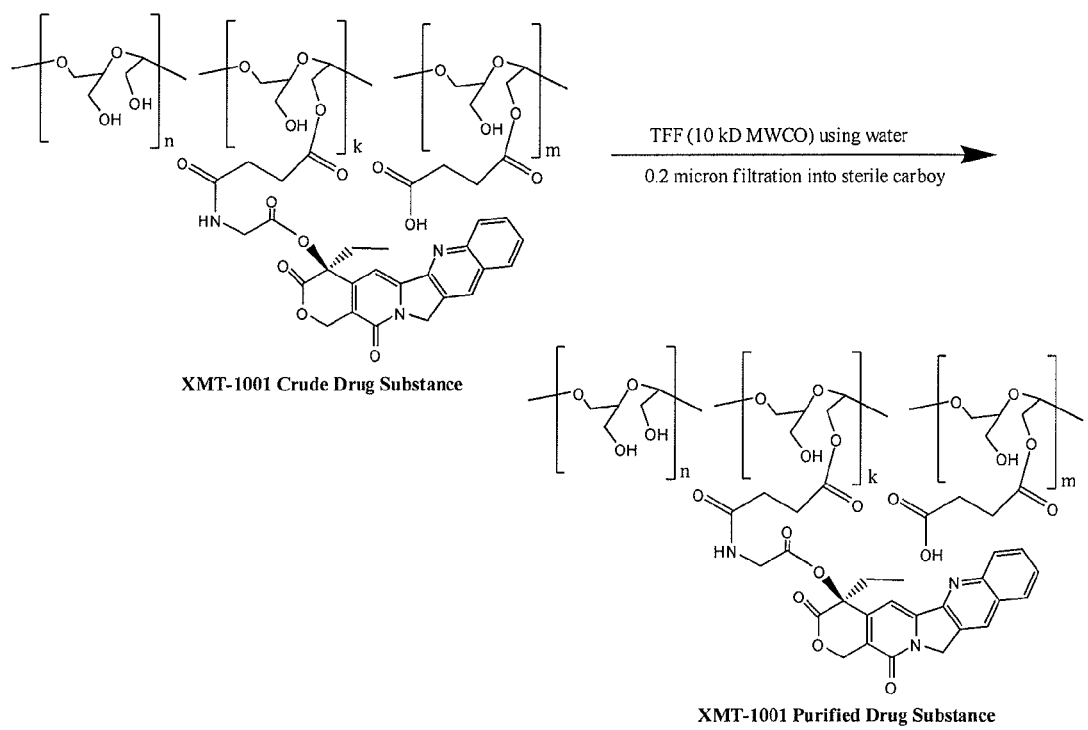
FIG. 10 is a diagram illustrating the final purification of the CPT-polymer conjugate.

Phase 6—Final Purification of the Aqueous PHF-CPT Conjugate (FIG. 10)

The crude aqueous PHF-CPT conjugate was first purified to remove particulates by passing it through a 0.1 micron or a 0.2 micron TFF filter, followed by purification (removal of low MW reagents and substances) by TFF using a filter having a nominal MWCO of 10,000 Daltons. Alternatively, membrane diafiltration was used instead of TFF.

Figure 11:
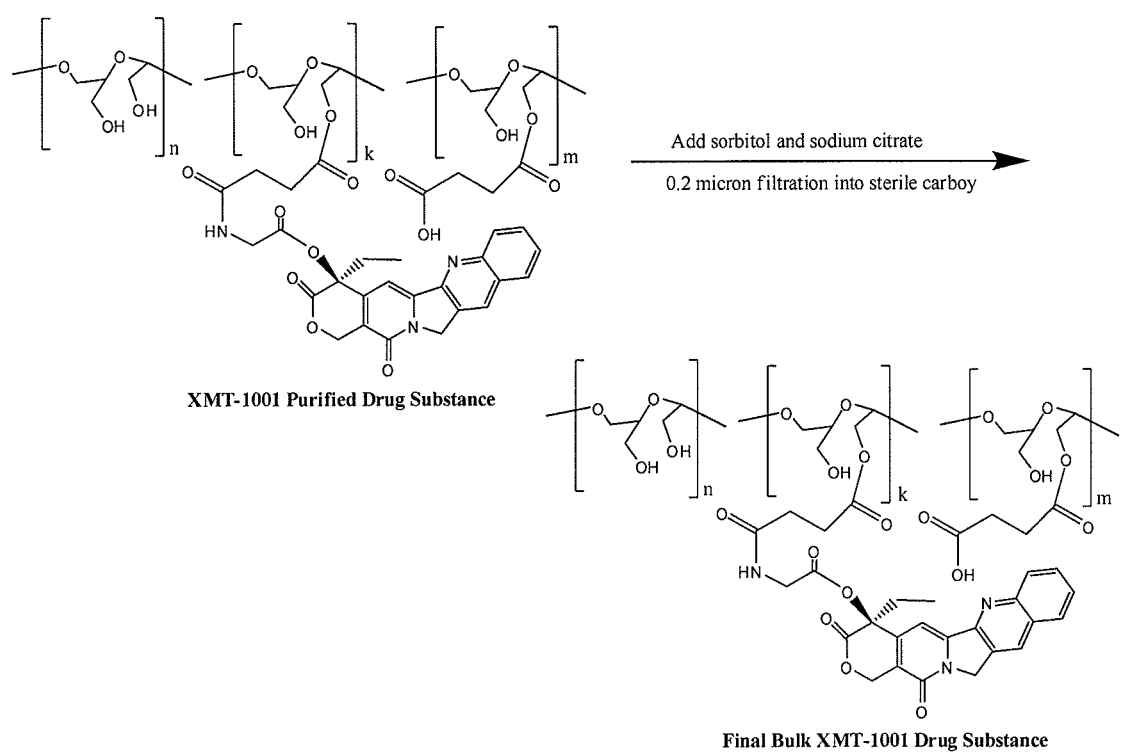
FIG. 11 is a diagram illustrating the formulation and final filtration of the CPT-polymer conjugate.

Phase 7—Formulation and Final Filtration of the Aqueous PHF-CPT Conjugate (FIG. 11)

The aqueous PHF-CPT conjugate was formulated with water for injection, and buffers, stabilizing agents, and/or other additives disclosed herein, to yield the bulk aqueous conjugate. These excipients were added within 24 hours of completing Phase 6 (excipients should always be added within 24 hours of completing Phase 6). The formulated PHF-CPT conjugate was then 0.2 micron filtered and packaged in sterile 20-liter polycarbonate carboy and stored at 2° C. to 8° C., protected from light.

Production of Lyophilized PHF-CPT Conjugate

Phase 8—Lyophilized Formulation: Vial Filling, Lyophilization, and Sealing

Each vial (20 mL) was filled with about 6 mL of the aqueous PHF-CPT conjugate from Phase 7 above, and then lyophilized to generate lyophilized cakes. The material was frozen by gradually decreasing the temperature to −50° C., and was then held at −50° C. for 2 hours. A vacuum was applied to the material and the temperature was gradually increased to −35° C., and was then held at −35° C. for about 60 hours. The material was then lyophilized at −5° C. for about 40 hours, and then at +15° C. for about 15 hours. After the lyophilization cycle was finished, the vials were sealed under nitrogen.

Alternate Phase 8—Lyophilized Formulation: Vial Filling, Lyophilization, and Sealing Each vial (30 mL) was filled with about 9 mL of the aqueous PHF-CPT conjugate from Phase 7 above, and then lyophilized to generate lyophilized cakes. The material was frozen by gradually decreasing the temperature to −45° C., and was then held at −45° C. for 2 hours. A vacuum was applied to the material and the temperature was gradually increased to −15° C., and was then held at −15° C. for about 60 hours. The material was then lyophilized at −5° C. for about 4 hours, and then at +15° C. for about 21 hours. After the lyophilization cycle was finished, the vials were stopped to 95% atmosphere with pure nitrogen.

EXPERIMENTAL

Example 1

Stability of Aqueous Solution of CPT-Polymer Conjugate—Effects of Temperature and pH Aliquots of 60 mg/mL aqueous CPT-polymer conjugate were formulated at pH 4.0 and 5.2, and were stored at 5° C., 20° C. and 40° C. These composition of these aliquots is described in Table 1 below. These aliquots were tested at 0, 1, 3, 6, 10, 12, and 26 day time points using reverse-phase HPLC.

TABLE 1

Composition of Formulated Aqueous CPT-Polymer Conjugate with Sorbitol

| Component | Approximate Weight % |
|---|---|
| CPT equivalents | 0.6% |
| CPT-polymer conjugate | 11.7% |
| Sorbitol | 85.8% |
| Sodium citrate | 2.5% |

Figure 3:
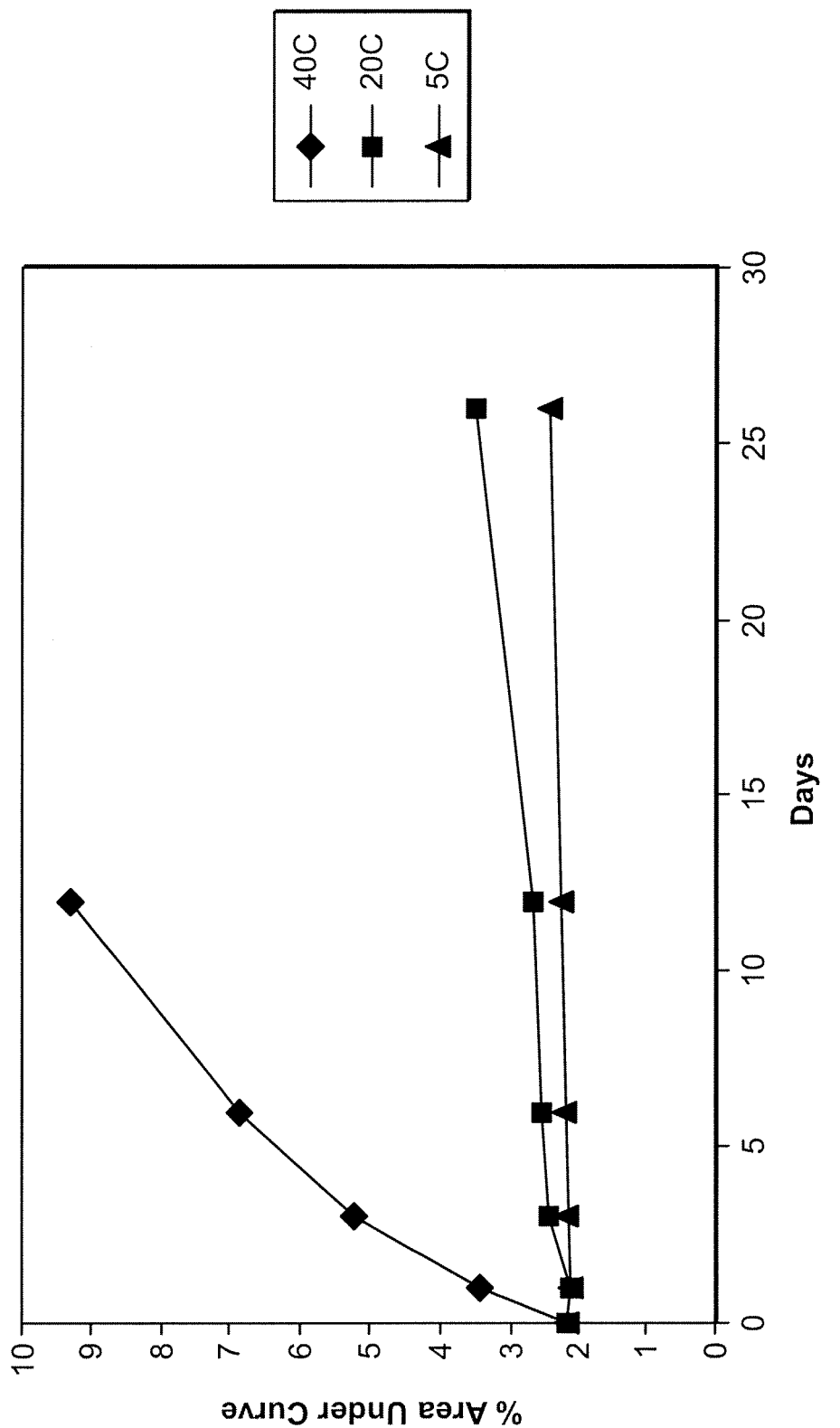
FIG. 3 is a graph depicting the stability of the CPT-polymer conjugate as liquid bulk stored for 26 days at pH 4.0 and varying temperatures. The result is expressed as percent area under the curve of the degradation product CPT-SI compared to overall response for the CPT-polymer conjugate.
Figure 4:
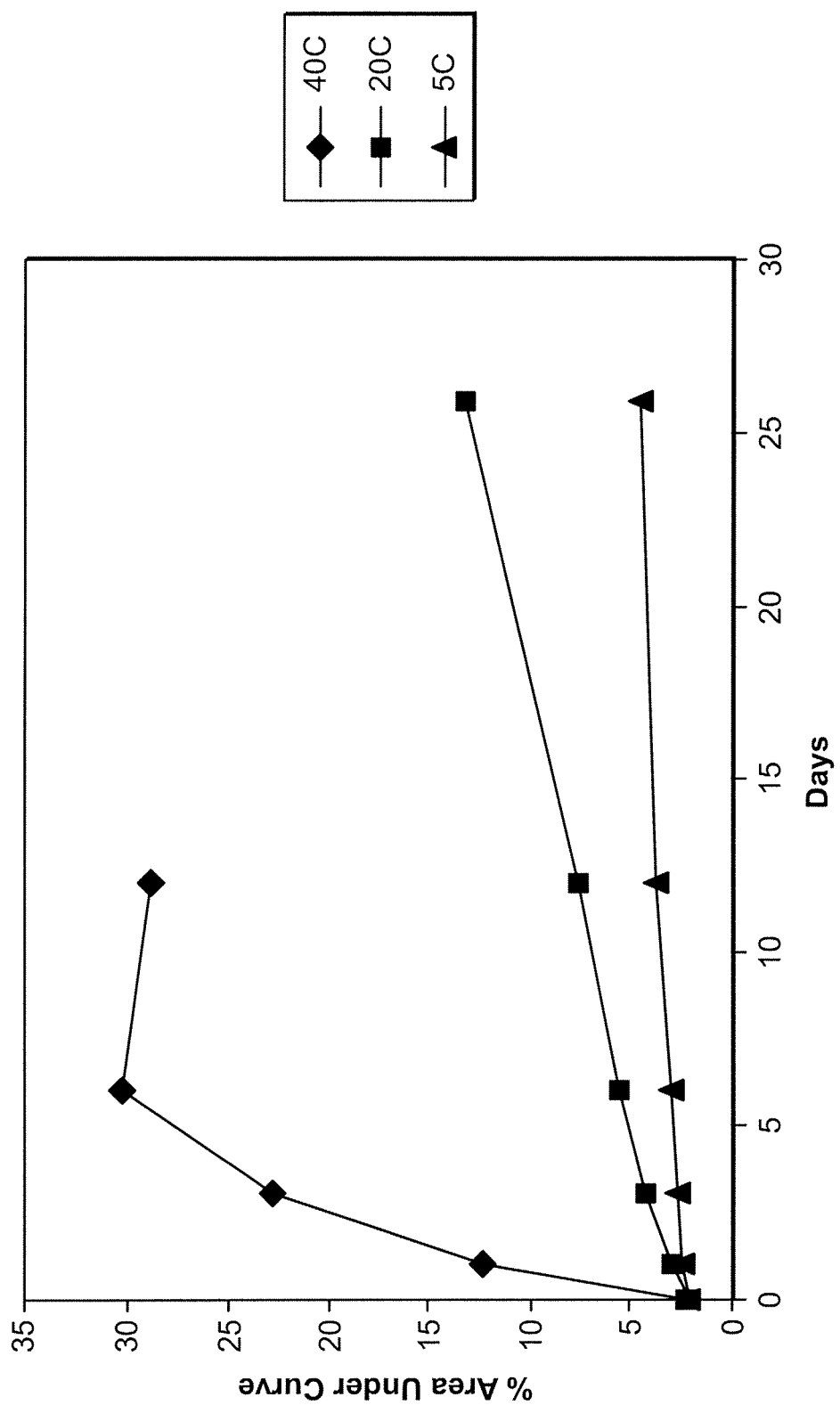
FIG. 4 is a graph depicting the stability of the CPT-polymer conjugate as liquid bulk stored for 26 days at pH 5.2 and varying temperatures. The result is expressed as percent area under the curve of the degradation product CPT-SI compared to overall response for the conjugate.

As shown in FIGS. 3 and 4, CPT-SI release was dependent upon pH and temperature. The CPT-polymer conjugate degrades when stored as an aqueous solution, primarily via hydrolysis, and releases CPT-SI into solution. The observed increase in CPT-SI over time thus indicates degradation of the CPT-polymer conjugate. Low pH and temperature are therefore the preferred storage conditions for the aqueous CPT-polymer conjugate.

Example 2

Stability of Aqueous Solution of CPT-Polymer Conjugate at pH 4.4 to 4.6

An aqueous solution of CPT-polymer conjugate was made according to Table 1 above, and maintained at pH 4.6 by sodium citrate buffer. The aqueous solution of CPT-polymer conjugate was stored at 2-8° C. and tested at 0, 15, 30, 45, 60, and 90 day time points using reverse-phase HPLC and HPSEC. The amounts of free CPT, CPT-SA, and CPT-SI in solution and the molecular weight distributions were comparable at time 0 and after 90 days. Thus an aqueous solution of CPT-polymer conjugate buffered to pH 4.6 is storage stable for at least 90 days. These results are summarized in Table 2.

TABLE 2

Stability of Aqueous CPT-polymer Conjugate at pH 4.6

| Time (days) | Free CPT (% total AUC) | CPT-SA (% total AUC) | CPT-SI (% total AUC) |
|---|---|---|---|
| 0 | <0.05 | <0.05 | <0.05 |
| 15 | <0.05 | <0.05 | <0.05 |
| 30 | <0.05 | <0.05 | <0.05 |
| 45 | <0.05 | <0.05 | <0.05 |
| 60 | <0.05 | <0.05 | <0.05 |
| 90 | <0.05 | <0.05 | <0.05 |

Example 3

Loading of CPT onto the Polymer Backbone at 1%, 5%, and 10%

To load approximately 1% CPT by weight onto the polymer backbone, couple each gram of CPT-Gly-TFA with 65±6 g of PHF-SA by the procedure described in the examples section under "Phase 5—Coupling of PHF-SA and CPT-glycine TFA".

To load approximately 5% CPT by weight onto the polymer backbone, couple each gram of CPT-Gly-TFA with 12±1 g of PHF-SA by the procedure described in the examples section under "Phase 5—Coupling of PHF-SA and CPT-glycine-TFA".

To load approximately 10% CPT by weight onto the polymer backbone, couple each gram of CPT-Gly-TFA with 5.5±0.5 g of PHF-SA by the procedure described in the examples section under "Phase 5—Coupling of PHF-SA and CPT-glycine TFA".

Example 4

Sorbitol Formulation

An aqueous solution of CPT-polymer conjugate was formulated with 85% sorbitol and 2.5% sodium citrate as shown in Table 3, and then lyophilized. The lyophilized vials were stored at 2-8° C. Each vial contained about 695 mg of the CPT-polymer conjugate. Vials were reconstituted with 15 mL sterile water for injection and tested at 0, 1, 3, and 6 month time points for molecular weight, free % SA, pH, osmolality, particle matter (HPSEC), other impurities (RP-HPLC), and free CPT, CPT-SA, and CPT-SI. The results are summarized in Table 4.

TABLE 3

Formulation with Sorbitol as a Stabilizing Agent

| Component | mg/vial | % weight | Concentration before lyophilization (mg/mL) |
| --- | --- | --- | --- |
| CPT-polymer conjugate | 78 | 11.7 | 13.0 |
| Sorbitol | 574 | 85.8 | 95.7 |
| Sodium citrate | 17 | 2.5 | 2.8 |

TABLE 4

Stability Results for Lyophilized Sorbitol Formulation

| | Time Point (months) at 2-8° C. | | | | | | |
| --- | --- | --- | --- | --- | --- | --- | --- |
| Assay | 0 | | 1 | | 3 | | 6 |
| Mw (KDa) | 334 | | 459 | | 338 | | 413 |
| Free SA (%) | 0.2 | | 0.2 | | 0.2 | | 0.2 |
| pH | 4.7 | | 4.6 | | 4.7 | | 4.7 |
| Osmolality (mOsm/kg) | 207 | | 230 | | 218 | | 225 |
| Free CPT (%) | 0.03 | | 0.02 | | 0.03 | | 0.03 |
| CPT-SA (%) | 0.02 | | 0.02 | | 0.02 | | 0.02 |
| CPT-SI (%) | 0.04 | | 0.04 | | 0.04 | | 0.04 |
| Other Impurities | RRT 1.73 | % 0.01 | RRT — | % — | RRT — | % — | RRT — % — |

Example 5

Mannitol Formulations

Three aqueous solutions of CPT-polymer conjugate were formulated with 6.5% sodium citrate and 4.2% citric acid, and either 44.6% mannitol, 35% mannitol, or 34% mannitol with 2.7% Polysorbate 80 as shown in Tables 5, 6, and 7, and then lyophilized. The lyophilized vials were stored at 2-8° C. Each vial contained about 168 mg of the CPT-polymer conjugate. Each vial was reconstituted with 10 mL 0.9% Normal Saline and tested at 0, 0.5, and 1 month time points for molecular weight. The results are summarized in Table 8.

TABLE 5

Mannitol Formulation #1 (44.6% mannitol)

| Component | mg/vial | % (weight) | Concentration before lyophilization (mg/mL) |
| --- | --- | --- | --- |
| PHF-CPT | 75 | 44.6 | 6.3 |
| Mannitol | 75 | 44.6 | 6.3 |
| Sodium citrate | 11 | 6.5 | 0.9 |
| Citric acid | 7 | 4.2 | 0.6 |

TABLE 6

Mannitol Formulation #2 (35% mannitol)

| Component | mg/vial | % (weight) | Concentration before lyophilization (mg/mL) |
| --- | --- | --- | --- |
| PHF-CPT | 75 | 52.4 | 6.4 |
| Mannitol | 50 | 35.0 | 4.3 |
| Sodium citrate | 11 | 7.7 | 0.9 |
| Citric acid | 7 | 4.9 | 0.6 |

TABLE 7

Mannitol Formulation #3 (34% mannitol + 2.7% Polysorbate 80)

| Component | mg/vial | % (weight) | Concentration before lyophilization (mg/mL) |
| --- | --- | --- | --- |
| PHF-CPT | 75 | 51.0 | 6.2 |
| Mannitol | 50 | 34.0 | 4.1 |
| Sodium citrate | 11 | 7.5 | 0.9 |
| Citric acid | 7 | 4.8 | 0.6 |
| Polysorbate 80 | 4 | 2.7 | 0.3 |

TABLE 8

Stability Results for Lyophilized Mannitol Formulations #1, #2, and #3 at 2-8° C.

| Formulation | Time point (months) | Mw (kD) | D90 (kD) | D50 (kD) | D10 (kD) |
| --- | --- | --- | --- | --- | --- |
| Formulation #1 (44.6% mannitol) | 0 | 191 | 415 | 108 | 38 |
| | 0.5 | 197 | 426 | 109 | 38 |
| | 1 | 200 | 437 | 114 | 39 |
| Formulation #2 (35% mannitol) | 0 | 186 | 409 | 107 | 38 |
| | 0.5 | 189 | 410 | 107 | 38 |
| | 1 | 203 | 437 | 114 | 39 |
| Formulation #3 (34% mannitol + 2.7% polysorbate 80) | 0 | 186 | 409 | 107 | 38 |
| | 0.5 | 187 | 405 | 106 | 38 |
| | 1 | 199 | 417 | 110 | 38 |

In a second study, two aqueous solutions of CPT-polymer conjugate were formulated with mannitol and Polysorbate 80 as shown in Tables 9 and 10. A portion of each aqueous solution was stored as a liquid in 30 mL PETG sterile square media bottles, and another portion was lyophilized in vials. The liquid material and the lyophilized vials were stored at 2-8° C. The liquid material was tested at 0, 0.5, 1, 2, 3, 4, and 6 month time points for molecular weight and impurities. The results are summarized in Tables 11 and 12. Each lyophilized vial was reconstituted with 0.9% Normal Saline and tested at 0, 1, 3, and 6 month time points for molecular weight and impurities. The results are summarized in Tables 13 and 14.

TABLE 9

Mannitol Formulation #4 (30 mg/mL PHF-CPT, 34.6% mannitol, and 1.0% Polysorbate 80)

| Component | Approximate Weight % | Concentration before lyophilization (mg/mL) |
|---|---|---|
| CPT equivalents | 3.1% | 1.8 |
| CPT-polymer conjugate | 51.9% | 30.0 |
| Mannitol | 34.6% | 20.0 |
| Sodium citrate | 7.6% | 4.4 |
| Citric acid | 4.8% | 2.8 |
| Polysorbate 80 | 1.0% | 0.6 |

TABLE 10

Mannitol Formulation #5 (15 mg/mL PHF-CPT, 34.6% mannitol, and 1.0% Polysorbate 80)

| Component | Approximate Weight % | Concentration before lyophilization (mg/mL) |
|---|---|---|
| CPT equivalents | 3.1% | 0.9 |
| CPT-polymer conjugate | 51.9% | 15.0 |
| Mannitol | 34.6% | 10 |
| Sodium citrate | 7.6% | 2.2 |
| Citric acid | 4.8% | 1.4 |
| Polysorbate 80 | 1.0% | 0.3 |

TABLE 11

Stability Results for Liquid Mannitol Formulation #4 (30 mg/mL PHF-CPT) at 2-8° C.

| Time point (months) | SEC (kD) | Impurity (% AUC) |
|---|---|---|
| 0 | Mw: 75<br>D90: 138<br>D50: 62<br>D10: 26 | Free CPT: 0.06%<br>CPT-SA: 0.05%<br>CPT-SI: 0.08% |
| 0.5 | Mw: 77<br>D90: 144<br>D50: 63<br>D10: 24 | Free CPT: 0.05%<br>CPT-SA: 0.05%<br>CPT-SI: 0.09% |
| 1 | Mw: 73<br>D90: 134<br>D50: 61<br>D10: 25 | Free CPT: 0.06%<br>CPT-SA: 0.06%<br>CPT-SI: 0.11% |
| 2 | Mw: 75<br>D90: 137<br>D50: 60<br>D10: 24 | Free CPT: 0.08%<br>CPT-SA: 0.07%<br>CPT-SI: 0.13% |
| 3 | Mw: 68<br>D90: 129<br>D50: 55<br>D10: 20 | Free CPT: 0.12%<br>CPT-SA: 0.09%<br>CPT-SI: 0.17% |
| 4 | Mw: 66<br>D90: 129<br>D50: 53<br>D10: 19 | Free CPT: 0.16%<br>CPT-SA: 0.11%<br>CPT-SI: 0.20% |
| 6 | Mw: 64<br>D90: 121<br>D50: 53<br>D10: 18 | Free CPT: 0.15%<br>CPT-SA: 0.11%<br>CPT-SI: 0.21% |

TABLE 12

Stability Results for Liquid Mannitol Formulation #5 (15 mg/mL PHF-CPT) at 2-8° C.

| Time point (months) | SEC (kD) | Impurity (% AUC) |
|---|---|---|
| 0 | Mw: 73<br>D90: 133<br>D50: 61<br>D10: 25 | Free CPT: 0.06%<br>CPT-SA: 0.05%<br>CPT-SI: 0.07% |
| 0.5 | Mw: 76<br>D90: 139<br>D50: 62<br>D10: 24 | Free CPT: 0.05%<br>CPT-SA: 0.05%<br>CPT-SI: 0.09% |
| 1 | Mw: 72<br>D90: 134<br>D50: 61<br>D10: 25 | Free CPT: 0.06%<br>CPT-SA: 0.06%<br>CPT-SI: 0.11% |
| 2 | Mw: 80<br>D90: 142<br>D50: 63<br>D10: 30 | Free CPT: 0.09%<br>CPT-SA: 0.07%<br>CPT-SI: 0.14% |
| 3 | Mw: 68<br>D90: 129<br>D50: 55<br>D10: 20 | Free CPT: 0.12%<br>CPT-SA: 0.09%<br>CPT-SI: 0.18% |
| 4 | Mw: 66<br>D90: 129<br>D50: 52<br>D10: 19 | Free CPT: 0.16%<br>CPT-SA: 0.10%<br>CPT-SI: 0.20% |
| 6 | Mw: 63<br>D90: 121<br>D50: 51<br>D10: 18 | Free CPT: 0.15%<br>CPT-SA: 0.11%<br>CPT-SI: 0.22% |

TABLE 13

Stability Results for Lyophilized Mannitol Formulation #4 (30 mg/mL PHF-CPT) at 2-8° C.

| Time point (months) | SEC (kD) | Impurity |
|---|---|---|
| 0 | Mw: 79<br>D90: 144<br>D50: 63<br>D10: 26 | Free CPT: 0.03%<br>CPT-SA: 0.04%<br>CPT-SI: 0.07% |
| 1 | Mw: 78<br>D90: 149<br>D50: 64<br>D10: 25 | Free CPT: 0.03%<br>CPT-SA: 0.04%<br>CPT-SI: 0.07% |
| 3 | Mw: 81<br>D90: 151<br>D50: 63<br>D10: 25 | Free CPT: 0.03%<br>CPT-SA: 0.04%<br>CPT-SI: 0.07% |
| 6 | Mw: 82<br>D90: 156<br>D50: 64<br>D10: 25 | Free CPT: 0.03%<br>CPT-SA: 0.04%<br>CPT-SI: 0.07% |

TABLE 14

Stability Results for Lyophilized Mannitol Formulation #5
(15 mg/mL PHF-CPT) at 2-8° C.

| Time point (months) | SEC (kD) | Impurity |
|---|---|---|
| 0 | Mw: 76<br>D90: 139<br>D50: 62<br>D10: 25 | Free CPT: 0.03%<br>CPT-SA: 0.04%<br>CPT-SI: 0.07% |
| 1 | Mw: 77<br>D90: 144<br>D50: 64<br>D10: 25 | Free CPT: 0.03%<br>CPT-SA: 0.04%<br>CPT-SI: 0.07% |
| 3 | Mw: 80<br>D90: 151<br>D50: 63<br>D10: 25 | Free CPT: 0.03%<br>CPT-SA: 0.04%<br>CPT-SI: 0.07% |
| 6 | Mw: 82<br>D90: 156<br>D50: 64<br>D10: 24 | Free CPT: 0.03%<br>CPT-SA: 0.03%<br>CPT-SI: 0.07% |

In a third study, PHF-CPT was formulated as described in Table 15 below, then lyophilized in vials and stored at stored at 2-8° C. Each lyophilized vial was reconstituted with 10 mL 0.45% Normal Saline and tested at 0, 3, 6, 9, and 13 month time points for molecular weight and impurities. The results are summarized in Table 16.

TABLE 15

Mannitol Formulation #6 (15 mg/mL PHF-CPT,
34.6% sorbitol, and 1% Polysorbate 80)

| Component | Approximate Weight % | Concentration before lyophilization (mg/mL) |
|---|---|---|
| CPT equivalents | 3.1% | 0.9 |
| CPT-polymer conjugate | 51.9% | 15.5 |
| Mannitol | 34.6% | 10.3 |
| Sodium citrate | 7.6% | 2.3 |
| Citric acid | 4.8% | 1.5 |
| Polysorbate 80 | 1.0% | 0.3 |

Example 5

Reconstitution Studies

The time required for reconstitution was determined for the lyophilized formulations described in Table 17 below, using the method described above. The samples were formulated in water as follows.

75 mg PHF-CPT, 100 mg mannitol formulation: In a 20 mL vial, 10.0 mL 7.5 mg/mL PHF-CPT solution was mixed with 1.0 mL 100 mg/mL mannitol solution and 0.5 mL 50 mg/mL sodium citrate solution.

75 mg PHF-CPT, 75 mg mannitol formulation: In a 20 mL vial, 10.0 mL 7.5 mg/mL PHF-CPT solution was mixed with 0.75 mL 100 mg/mL mannitol solution and 0.5 mL 50 mg/mL sodium citrate solution.

75 mg PHF-CPT, 50 mg mannitol formulation: In a 20 mL vial, 10.0 mL 7.5 mg/mL PHF-CPT solution was mixed with 0.5 mL 100 mg/mL mannitol solution and 0.5 mL 50 mg/mL sodium citrate solution.

75 mg PHF-CPT, 50 mg mannitol, 15 mg Polysorbate 80 formulation: In a 20 mL vial, 10.0 mL 7.5 mg/mL PHF-CPT solution was mixed with 0.5 mL 100 mg/mL mannitol solution, 0.5 mL 50 mg/mL sodium citrate solution and 0.5 mL 30 mg/mL Polysorbate solution.

The solutions were then lyophilized in vials and stored at 2-8° C. Each lyophilized vial was reconstituted with water or 0.9% Normal Saline, as indicated in Table 17, and gently shaken until all solids dissolved. The results are summarized in Table 17.

TABLE 17

Reconstitution Study # 1

| Formulation | Solubility in Water (minutes) | Solubility in Saline (minutes) |
|---|---|---|
| 75 mg PHF-CPT<br>100 mg mannitol | 3<br>(15 mL water) | 2<br>(5 mL saline) |
| 75 mg PHF-CPT<br>75 mg mannitol | 3<br>(15 mL water) | 2<br>(5 mL saline) |
| 75 mg PHF-CPT | 7 | 5 |

TABLE 16

Stability Data for Mannitol Formulation #6 After Lyophilization

| Test (Method) | Stability Interval (months) | | | | |
|---|---|---|---|---|---|
| | 0 | 3 | 6 | 9 | 13 |
| Reconstitution Time (minutes:seconds) | 1:39 | 1:32 | 1:34 | 1:55 | 0:36 |
| Molecular Weight Analysis/Distribution (SEC (kDa)) | Mw: 105<br>$D_{10}$: 23<br>$D_{50}$: 59<br>$D_{90}$: 193 | Mw: 120<br>$D_{10}$: 20<br>$D_{50}$: 60<br>$D_{90}$: 214 | Mw: 104<br>$D_{10}$: 22<br>$D_{50}$: 57<br>$D_{90}$: 196 | Mw: 104<br>$D_{10}$: 18<br>$D_{50}$: 59<br>$D_{90}$: 199 | Mw: 105<br>$D_{10}$: 26<br>$D_{50}$: 65<br>$D_{90}$: 186 |
| % CPT Loading (UV) | 6.1 | 6.0 | 6.0 | 6.0 | 6.2 |
| Free SA (%) (RP-HPLC) | 0.0 | 0.0 | 0.0 | 0.0 | 0.0 |
| Osmolality (mOsm/kg) | 340 | 333 | 333 | 335 | 334 |
| Unbound CPT and Impurities (RP-HPLC weight %) | CPT: 0.09<br>CPT-SA: 0.21<br>CPT-SI: 0.05<br>CPY-Gly: 0.21 | CPT: 0.09<br>CPT-SA: 0.21<br>CPT-SI: 0.06<br>CPY-Gly: 0.16 | CPT: 0.09<br>CPT-SA: 0.21<br>CPT-SI: 0.05<br>CPY-Gly: 0.19 | CPT: 0.09<br>CPT-SA: 0.24<br>CPT-SI: 0.05<br>CPY-Gly: 0.20 | CPT: 0.10<br>CPT-SA: 0.18<br>CPT-SI: 0.07<br>CPY-Gly: 0.19 |

TABLE 17-continued

Reconstitution Study # 1

| Formulation | Solubility in Water (minutes) | Solubility in Saline (minutes) |
|---|---|---|
| 50 mg mannitol<br>75 mg PHF-CPT | (15 mL water)<br><1<br>(immediately) | (5 mL saline)<br><1<br>(immediately) |
| 50 mg mannitol<br>15 mg Polysorbate 80 | (5 mL water) | (5 mL saline) |

The time required for reconstitution was determined for the lyophilized formulations described in Table 18 below, using the method described above. The samples were formulated in water as follows.

75 mg PHF-CPT, 75 mg mannitol formulation: In a 20 mL vial, 10.0 mL 7.5 mg/mL PHF-CPT solution was mixed with 0.75 mL 100 mg/mL mannitol solution, 0.55 mL 20 mg/mL sodium citrate solution, and 0.6 mL 10 mg/mL citric acid solution.

75 mg PHF-CPT, 50 mg mannitol formulation: In a 20 mL vial, 10.0 mL 7.5 mg/mL PHF-CPT solution was mixed with 0.5 mL 100 mg/mL mannitol solution, 0.55 mL 20 mg/mL sodium citrate solution, and 0.6 mL 10 mg/mL citric acid solution.

75 mg PHF-CPT, 50 mg mannitol, 4 mg Polysorbate 80 formulation: In a 20 mL vial, 10.0 mL 7.5 mg/mL PHF-CPT solution was mixed with 0.5 mL 100 mg/mL mannitol solution, 0.55 mL 20 mg/mL sodium citrate solution, 0.6 mL 10 mg/mL citric acid solution and 0.5 mL 8 mg/mL Polysorbate solution.

The solutions were then lyophilized in vials and stored at 2-8° C. Each lyophilized vial was reconstituted with 10 mL 0.9% Normal Saline and gently inverted 10 times, then allowed to stand until all solids were dissolved. The results are summarized in Table 18.

TABLE 18

Reconstitution Study #2

| Formulation | Time Point (months at 2-8° C.) | Solubility in 10 mL Saline (minutes) |
|---|---|---|
| 75 mg PHF-CPT<br>50 mg mannitol | 0<br>0.5 | 13<br>29 |
| 75 mg PHF-CPT<br>50 mg mannitol | 0<br>0.5 | 5<br><1 |
| 75 mg PHF-CPT<br>75 mg mannitol | 0<br>0.5 | 2<br>29 |

Example 6

Additional Formulation

The formulation described in Table 19 was made and filled in 30 mL vials, using 9 mL of aqueous PHF-CPT per vial. The vials were then lyophilized.

TABLE 19

30 mg/mL PHF-CPT Formulation with Mannitol and Polysorbate 80

| Component | Approximate Weight % | Concentration before lyophilization (mg/mL) |
|---|---|---|
| CPT equivalents | 3.1% | 1.9 |
| PHF-CPT | 51.9% | 30.5 |

TABLE 19-continued 30 mg/mL PHF-CPT Formulation with Mannitol and Polysorbate 80

| Component | Approximate Weight % | Concentration before lyophilization (mg/mL) |
|---|---|---|
| Mannitol | 34.6% | 20.3 |
| Sodium citrate | 7.6% | 4.5 |
| Citric acid | 4.8% | 2.8 |
| Polysorbate 80 | 1.0% | 0.6 |

Other Embodiments

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A pharmaceutical composition suitable for intravenous administration comprising a compound of formula (I):

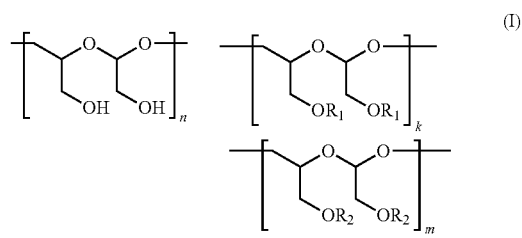

wherein one of $R_1$ is H or

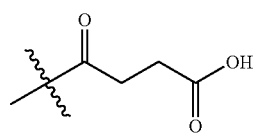 [SMILES: *C(=O)CCC(=O)O]

and the other is

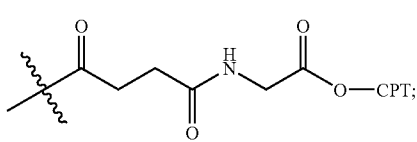

one of $R_2$ is H or

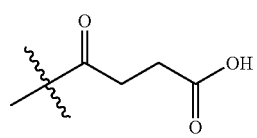 [SMILES: *C(=O)CCC(=O)O]

and the other is

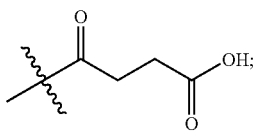 [SMILES: *C(=O)CCC(=O)O]

CPT is camptothecin;
n is 32-3320;
m is 0-833;
k is 1-216;
wherein k, m, and n are selected so that about 1% to about 15% of the compound by weight is camptothecin;
a stabilizing agent;
one or more buffers; and
a surfactant;
wherein the molecular weight of the compound is from about 10 kD to about 500 kD, and the pharmaceutical composition has a pH of about 4.0 to 5.2.

2. The pharmaceutical composition of claim 1, wherein about 4% to about 7% of the compound by weight is camptothecin.

3. The pharmaceutical composition of claim 2, wherein about 5% to about 6% of the compound by weight is camptothecin.

4. The pharmaceutical composition of claim 2, wherein about 6% of the compound by weight is camptothecin.

5. The pharmaceutical composition of claim 1, wherein the stabilizing agent is selected from the group consisting of sorbitol, mannitol, sucrose, lactose, glucose, xylitol, maltose, hydroxypropyl-β-cyclodextrin, lactitol, dextrose, glycerin, and maltitol.

6. The pharmaceutical composition of claim 5, wherein the stabilizing agent is sorbitol.

7. The pharmaceutical composition of claim 6, wherein the sorbitol is present at a concentration of about 1 mg/mL to about 500 mg/mL.

8. The pharmaceutical composition of claim 5, wherein the stabilizing agent is mannitol.

9. The pharmaceutical composition of claim 8, wherein the mannitol is present at a concentration of between about 1 mg/mL to about 500 mg/mL.

10. The pharmaceutical composition of claim 8, wherein the mannitol is present at a concentration of between about 1 mg/mL to about 200 mg/mL.

11. The pharmaceutical composition of claim 8, wherein the mannitol is present at a concentration of between about 1 mg/mL to about 25 mg/mL.

12. The pharmaceutical composition of claim 8, wherein the mannitol is present at a concentration of about 10.3 mg/mL.

13. The pharmaceutical composition of claim 8, wherein the mannitol is present at a concentration of about 20.3 mg/mL.

14. The pharmaceutical composition of claim 1, wherein the one or more buffers is selected from the group consisting of sodium citrate, ascorbate, succinate, lactate, citric acid, boric acid, borax, hydrochloric acid, disodium hydrogen phosphate, acetic acid, formic acid, glycine, bicarbonate, tartaric acid, Tris-glycine, Tris-NaCl, Tris-ethylenediamine tetraacetic acid, ("EDTA"), Tris-borate-EDTA, Tris-acteate-EDTA ("TAE") buffer and Tris-buffered saline, 4-(2-hydroxyethyl)-1-piperazineethanesulfonic acid ("HEPES"), 3-(N-morpholino)propanesulfonic acid ("MOPS"), piperazine-1,4-bis(2-ethanesulfonic acid) ("PIPES"), 2-(N-morpholino)ethanesulfonic acid ("MES"), phosphate buffered saline ("PBS"), saline-sodium citrate ("SSC"), saline-tris-EDTA ("STE"), and tris-magnesium.

15. The pharmaceutical composition of claim 14, wherein the one or more buffers includes sodium citrate.

16. The pharmaceutical composition of claim 14, wherein the one or more buffers includes sodium citrate and citric acid.

17. The pharmaceutical composition of claim 1, wherein the surfactant is selected from the group consisting of Polysorbate 80, Polysorbate 20, Poloxamer 407, Solutol HS 15, Poloxamer 188, sodium lauryl sulphate, ether sulphates, sulphated oils, cetrimide BP, benzalkonium chloride, lecithin, cetromacrogel 1000 BPC, and alkali metal soaps of the formula RCOOX where R=C10-C20 alkyl group, and X=sodium, potassium, or ammonium.

18. The pharmaceutical composition of claim 17, wherein the surfactant is Polysorbate 80.

19. The pharmaceutical composition of claim 18, wherein the Polysorbate 80 is present at a concentration of between about 0.1 mg/mL to about 10 mg/mL.

20. The pharmaceutical composition of claim 19, wherein the Polysorbate 80 is present at a concentration of between about 0.1 mg/mL and about 4.5 mg/mL.

21. The pharmaceutical composition of claim 20, wherein the Polysorbate 80 is present at a concentration of about 0.1 mg/mL to about 1.0 mg/mL.

22. The pharmaceutical composition of claim 1, wherein the pharmaceutical composition is a storage stable aqueous solution.

23. The pharmaceutical composition of claim 1, wherein the pharmaceutical composition is a highly storage stable aqueous solution.

24. The pharmaceutical composition of claim 1, wherein the composition is a lyophilized cake suitable for intravenous administration after reconstitution.

25. The pharmaceutical composition of claim 1, wherein the pharmaceutical composition is storage stable and the pH of the pharmaceutical composition is about 4.2 to about 4.8.

26. The pharmaceutical composition of claim 25, wherein about 4% to about 7% of the compound by weight is camptothecin.

27. The pharmaceutical composition of claim 25, wherein about 5% to about 6% of the compound by weight is camptothecin.

28. The pharmaceutical composition of claim 25, wherein about 6% of the compound by weight is camptothecin.

29. The pharmaceutical composition of claim 25, wherein the one or more buffers are selected from the group consisting of sodium citrate, ascorbate, succinate, lactate, citric acid, boric acid, borax, hydrochloric acid, disodium hydrogen phosphate, acetic acid, formic acid, glycine, bicarbonate, tartaric acid, Tris-glycine, Tric-NaCl, Tris-ethylenediamine tetraacetic acid, ("EDTA"), Tris-borate-EDTA, Tris-acteate-EDTA ("TAE") buffer and Tris-buffered saline, 4-(2-hydroxyethyl)-1-piperazineethanesulfonic acid ("HEPES"), 3-(N-morpholino)propanesulfonic acid ("MOPS"), piperazine-1,4-bis(2-ethanesulfonic acid) ("PIPES"), 2-(N-morpholino)ethanesulfonic acid ("MES"), phosphate buffered saline ("PBS"), saline-sodium citrate ("SSC"), saline-tris-EDTA ("STE"), and tris-magnesium.

30. The pharmaceutical composition of claim 29, wherein the one or more buffers includes sodium citrate.

31. The pharmaceutical composition of claim 29, wherein the buffer one or more buffers sodium citrate and citric acid.

32. The pharmaceutical composition of claim 25, wherein the stabilizing agent is selected from the group consisting of sorbitol, mannitol, sucrose, lactose, glucose, xylitol, maltose, hydroxypropyl-β-cyclodextrin, lactitol, dextrose, glycerin, and maltitol.

33. The pharmaceutical composition of claim 32, wherein the stabilizing agent is sorbitol.

34. The pharmaceutical composition of claim 33, wherein the concentration of sorbitol is about 1 mg/mL to about 500 mg/mL.

35. The pharmaceutical composition of claim 32, wherein the stabilizing agent is mannitol.

36. The pharmaceutical composition of claim 35, wherein the concentration of mannitol is about 1 mg/mL to about 500 mg/mL.

37. The pharmaceutical composition of claim 35, wherein the concentration of mannitol is about 1 mg/mL to about 200 mg/mL.

38. The pharmaceutical composition of claim 35, wherein the concentration of mannitol is about 1 mg/mL to about 25 mg/mL.

39. The pharmaceutical composition of claim 35, wherein the concentration of mannitol is about 10.3 mg/mL.

40. The pharmaceutical composition of claim 35, wherein the concentration of mannitol is about 20.3 mg/mL.

41. The pharmaceutical composition of claim 25, wherein the surfactant is selected from the group consisting of Polysorbate 80, Polysorbate 20, Poloxamer 407, Solutol HS 15, Poloxamer 188, sodium lauryl sulphate, ether sulphates, sulphated oils, cetrimide BP, benzalkonium chloride, lecithin, cetromacrogel 1000 BPC, and alkali metal soaps of the formula RCOOX where R=C10-C20 alkyl group, and X=sodium, potassium, or ammonium.

42. The pharmaceutical composition of claim 41, wherein the surfactant is Polysorbate 80.

43. The pharmaceutical composition of claim 42, wherein the concentration of Polysorbate 80 is between about 0.1 mg/mL to about 10 mg/mL.

44. The pharmaceutical composition of claim 42, wherein the concentration of Polysorbate 80 is between about 0.1 mg/mL and about 4.5 mg/mL.

45. The pharmaceutical composition of claim 42, wherein the concentration of Polysorbate 80 is about 0.1 mg/mL to about 1.0 mg/mL.

46. The pharmaceutical composition of claim 25, wherein the pharmaceutical composition is highly storage stable.

47. The pharmaceutical composition of claim 1, wherein the pharmaceutical composition is suitable for lyophilization and reconstitution.

48. The pharmaceutical composition of claim 47, wherein about 4% to about 7% of the compound by weight is camptothecin.

49. The pharmaceutical composition of claim 47, wherein about 5% to about 6% of the compound by weight is camptothecin.

50. The pharmaceutical composition of claim 47, wherein about 6% of the compound by weight is camptothecin.

51. The pharmaceutical composition of claim 47, wherein the stabilizing agent is selected from the group consisting of sorbitol, mannitol, sucrose, lactose, glucose, xylitol, maltose, hydroxypropyl-β-cyclodextrin, lactitol, dextrose, glycerin, and maltitol.

52. The pharmaceutical composition of claim 51, wherein the stabilizing agent is sorbitol.

53. The pharmaceutical composition of claim 52, wherein the sorbitol is present at a concentration of between about 1 mg/mL and about 500 mg/mL.

54. The pharmaceutical composition of claim 51, wherein the stabilizing agent is mannitol.

55. The pharmaceutical composition of claim 54, wherein mannitol is present in the pharmaceutical composition at a concentration of between about 1 mg/mL to about 500 mg/mL.

56. The pharmaceutical composition of claim 54, wherein mannitol is present in the pharmaceutical composition at a concentration of between about 1 mg/mL to about 200 mg/mL.

57. The pharmaceutical composition of claim 54, wherein mannitol is present in the pharmaceutical composition at a concentration of between about 1 mg/mL to about 25 mg/mL.

58. The pharmaceutical composition of claim 54, wherein mannitol is present in the pharmaceutical composition at a concentration of about 10.3 mg/mL.

59. The pharmaceutical composition of claim 54, wherein mannitol is present in the pharmaceutical composition at a concentration of about 20.3 mg/mL.

60. The pharmaceutical composition of claim 47, wherein the one or more buffers is selected from the group consisting of sodium citrate, ascorbate, succinate, lactate, citric acid, boric acid, borax, hydrochloric acid, disodium hydrogen phosphate, acetic acid, formic acid, glycine, bicarbonate, tartaric acid, Tris-glycine, Tris-NaCl, Tris-ethylenediamine tetraacetic acid ("EDTA"), Tris-borate-EDTA, Tris-acteate-EDTA ("TAE") buffer and Tris-buffered saline, 4-(2-hydroxyethyl)-1-piperazineethanesulfonic acid ("HEPES"), 3-(N-morpholino)propanesulfonic acid ("MOPS"), piperazine-1,4-bis(2-ethanesulfonic acid) ("PIPES"), 2-(N-morpholino)ethanesulfonic acid ("MES"), phosphate buffered saline ("PBS"), saline-sodium citrate ("SSC"), saline-tris-EDTA ("STE"), and tris-magnesium.

61. The pharmaceutical composition of claim 60, wherein the one or more buffers includes sodium citrate.

62. The pharmaceutical composition of claim 60, wherein the one or more buffers includes sodium citrate and citric acid.

63. The pharmaceutical composition of claim 47, wherein the surfactant is selected from the group consisting of Polysorbate 80, Polysorbate 20, Poloxamer 407, Solutol HS 15, Poloxamer 188, sodium lauryl sulphate, ether sulphates, sulphated oils, cetrimide BP, benzalkonium chloride, lecithin, cetromacrogel 1000 BPC, and alkali metal soaps of the formula RCOOX where R=C10-C20 alkyl group, and X=sodium, potassium, or ammonium.

64. The pharmaceutical composition of claim 63, wherein the surfactant is Polysorbate 80.

65. The pharmaceutical composition of claim 64, wherein the concentration of Polysorbate 80 is from about 0.1 mg/mL to about 10 mg/mL.

66. The pharmaceutical composition of claim 65, wherein the concentration of Polysorbate 80 is from about 0.1 mg/mL and about 4.5 mg/mL.

67. The pharmaceutical composition of claim 65, wherein the concentration of Polysorbate 80 is about 0.1 mg/mL to about 1.0 mg/mL.

68. The pharmaceutical composition of claim 47, wherein the pharmaceutical composition is storage stable.

69. The pharmaceutical composition of claim 47, wherein the pharmaceutical composition is highly storage stable.

70. The pharmaceutical composition of claim 1, wherein the pharmaceutical composition is in the form of an injectable solution and is prepared using a liquid to reconstitute a lyophilized cake comprising the compound of formula (I).

71. The pharmaceutical composition of claim 70, wherein about 4% to about 7% by weight of the compound is CPT.

72. The pharmaceutical composition of claim 71, wherein about 5% to about 6% by weight of the compound is CPT.

73. The pharmaceutical composition of claim 71, wherein about 6% by weight of the compound is CPT.

74. The pharmaceutical composition of claim 70, wherein the stabilizing agent is selected from the group consisting of sorbitol, mannitol, sucrose, lactose, glucose, xylitol, maltose, hydroxypropyl-β-cyclodextrin, lactitol, dextrose, glycerin, and maltitol.

75. The pharmaceutical composition of claim 74, wherein the stabilizing agent is sorbitol.

76. The pharmaceutical composition of claim 75, wherein the concentration of sorbitol is about 1 mg/mL to about 500 mg/mL.

77. The pharmaceutical composition of claim 70, wherein the stabilizing agent is mannitol.

78. The pharmaceutical composition of claim 77, wherein the concentration of mannitol is between about 1 mg/mL to about 500 mg/mL.

79. The pharmaceutical composition of claim 77, wherein the concentration of mannitol is between about 1 mg/mL to about 200 mg/mL.

80. The pharmaceutical composition of claim 77, wherein the concentration of mannitol is between about 1 mg/mL to about 25 mg/mL.

81. The pharmaceutical composition of claim 77, wherein the concentration of mannitol is about 10.3 mg/mL.

82. The pharmaceutical composition of claim 77, wherein the concentration of mannitol is about 20.3 mg/mL.

83. The pharmaceutical composition of claim 70, wherein the surfactant is selected from the group consisting of Polysorbate 80, Polysorbate 20, Poloxamer 407, Solutol HS 15, Poloxamer 188, sodium lauryl sulphate, ether sulphates, sulphated oils, cetrimide BP, benzalkonium chloride, lecithin, cetromacrogel 1000 BPC, and alkali metal soaps of the formula RCOOX where R=C10-C20 alkyl group, and X=sodium, potassium, or ammonium.

84. The pharmaceutical composition of claim 83, wherein the surfactant is Polysorbate 80.

85. The pharmaceutical composition of claim 84, wherein the concentration of Polysorbate 80 is about 0.1 mg/mL to about 10 mg/mL.

86. The pharmaceutical composition of claim 85, wherein the concentration of Polysorbate 80 is from about 0.1 mg/mL and about 4.5 mg/mL.

87. The pharmaceutical composition of claim 85, wherein the concentration of Polysorbate 80 is about 0.1 mg/mL to about 1.0 mg/mL.

88. The pharmaceutical composition of claim 70, wherein the pH of the injectable solution is about 4.2 to about 4.8.

89. The pharmaceutical composition of claim 70, wherein the one or more buffers is selected from the group consisting of sodium citrate, ascorbate, succinate, lactate, citric acid, boric acid, borax, hydrochloric acid, disodium hydrogen phosphate, acetic acid, formic acid, glycine, bicarbonate, tartaric acid, Tris-glycine, Tris-NaCl, Tris-ethylenediamine tetraacetic acid ("EDTA"), Tris-borate-EDTA, Tris-acteate-EDTA ("TAE") buffer and Tris-buffered saline, 4-(2-hydroxyethyl)-1-piperazineethanesulfonic acid ("HEPES"), 3-(N-morpholino)propanesulfonic acid ("MOPS"), piperazine-1,4-bis(2-ethanesulfonic acid) ("PIPES"), 2-(N-morpholino)ethanesulfonic acid ("MES"), phosphate buffered saline ("PBS"), saline-sodium citrate ("SSC"), saline-tris-EDTA ("STE"), and tris-magnesium.

90. The pharmaceutical composition of claim 89, wherein the one or buffers includes sodium citrate.

91. The pharmaceutical composition of claim 89, wherein the one or more buffers includes sodium citrate and citric acid.

92. The pharmaceutical composition of claim 70, wherein the liquid is sterile water.

93. The pharmaceutical composition of claim 70, wherein the liquid is 0.9% Normal saline.

* * * * *